United States Patent [19]

Komada et al.

[11] Patent Number: 6,036,880
[45] Date of Patent: Mar. 14, 2000

[54] NIOBIUM-CONTAINING AQUEOUS SOLUTION FOR USE IN PRODUCING NIOBIUM-CONTAINING OXIDE-CATALYST

[75] Inventors: Satoru Komada, Yokohama; Hidenori Hinago, Kurashiki; Masatoshi Kaneta, Yokohama; Mamoru Watanabe, Kibi-gun, all of Japan

[73] Assignee: Asahi Kasei Kogyo Kabushiki Kaisha, Osaka, Japan

[21] Appl. No.: 09/129,412

[22] Filed: Aug. 5, 1998

[30] Foreign Application Priority Data

| Aug. 5, 1997 | [JP] | Japan | ................................... 9-222041 |
| Mar. 13, 1998 | [JP] | Japan | ................................... 10-080501 |

[51] Int. Cl.$^7$ .............................. C09K 3/00; B01J 23/16; C07C 253/00; C07C 51/16
[52] U.S. Cl. .................... 252/183.13; 502/353; 558/321; 562/547
[58] Field of Search ...................... 252/183.13; 502/353; 558/321; 562/547

[56] References Cited

U.S. PATENT DOCUMENTS

| 4,760,159 | 7/1988 | Suresh et al. . |
| 5,049,692 | 9/1991 | Hatano et al. . |
| 5,231,214 | 7/1993 | Ushikubo et al. . |
| 5,422,328 | 6/1995 | Ushikubo et al. . |

FOREIGN PATENT DOCUMENTS

| 0 767 164 A1 | 4/1997 | European Pat. Off. . |
| 0 529 853 B1 | 3/1993 | Japan . |
| 5-213848 | 8/1993 | Japan . |
| 6-227819 | 8/1994 | Japan . |
| 6-228073 | 8/1994 | Japan . |
| 6-279351 | 10/1994 | Japan . |
| 7-10801 | 1/1995 | Japan . |
| 7-144132 | 6/1995 | Japan . |
| 7-232071 | 9/1995 | Japan . |
| 7-289907 | 11/1995 | Japan . |
| 7-315842 | 12/1995 | Japan . |
| 8-57319 | 3/1996 | Japan . |
| 8-141401 | 6/1996 | Japan . |
| 9-316023 | 12/1997 | Japan . |
| 10-45664 | 2/1998 | Japan . |

*Primary Examiner*—Johann Richter
*Assistant Examiner*—Joseph Murray
*Attorney, Agent, or Firm*—Pennie & Edmonds LLP

[57] ABSTRACT

Disclosed is a niobium(Nb)-containing aqueous solution for use in producing a Nb-containing oxide catalyst, wherein the oxide catalyst comprises an oxide of a plurality of active component elements including Nb and is for use in a catalytic oxidation or ammoxidation of propane or isobutane in the gaseous phase, and wherein the oxide catalyst is prepared by a process comprising mixing the Nb-containing aqueous solution with (an) aqueous mixture(s) containing compounds of active component elements of the oxide catalyst other than Nb, to thereby provide an aqueous compound mixture, and drying the aqueous compound mixture, followed by calcination. The Nb-containing aqueous solution comprises water having dissolved therein a dicarboxylic acid, an Nb compound and optionally ammonia, wherein the dicarboxylic acid/Nb molar ratio ($\alpha$) satisfies: $1 \leq (\alpha) \leq 4$, and the ammonia/Nb molar ratio ($\beta$) satisfies: $0 \leq (\beta) \leq 2$. By the use of the niobium-containing aqueous solution, it has become possible to produce efficiently an oxide catalyst which, when used in a catalytic oxidation or ammoxidation of propane or isobutane in the gaseous phase, exhibits high catalytic activity, and which, therefore, can be advantageously used for producing (meth) acrylic acid or (meth)acrylonitrile in high yield.

20 Claims, No Drawings

NIOBIUM-CONTAINING AQUEOUS SOLUTION FOR USE IN PRODUCING NIOBIUM-CONTAINING OXIDE-CATALYST

BACKGROUND OF THE INVENTION

1. Field of the Invention

The present invention relates to a niobium-containing aqueous solution for use in producing a niobium-containing oxide catalyst. More particularly, the present invention is concerned with a niobium-containing aqueous solution for use in producing a niobium-containing oxide catalyst, wherein the oxide catalyst is for use in a catalytic oxidation or ammoxidation of propane or isobutane in the gaseous phase and is prepared by a process comprising mixing the niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination. The niobium-containing aqueous solution of the present invention comprises water having dissolved therein a dicarboxylic acid, a niobium compound and optionally ammonia, wherein the dicarboxylic acid and the niobium are present in a specific molar ratio, and the optional ammonia, if any, is present in a small amount. By the use of the niobium-containing aqueous solution of the present invention, it has become possible to produce efficiently an oxide catalyst which, when used in a catalytic oxidation or ammoxidation of propane or isobutane in the gaseous phase, exhibits high catalytic activity. Therefore, by the use of the oxide catalyst produced by using the niobium-containing aqueous solution of the present invention, (meth)acrylic acid or (meth)acrylonitrile can be produced in high yield. The present invention is also concerned with the oxide catalyst produced by using the niobium-containing aqueous solution of the present invention, and the use of the oxide catalyst.

2. Prior Art

There has been well known a process for producing (meth)acrylic acid by oxidation of propylene or isobutylene and a process for producing (meth)acrylonitrile by ammoxidation of propylene or isobutylene. Recently, as substitutes for such processes for the oxidation and ammoxidation of propylene or isobutylene, attention has been attracted to a process for producing (meth)acrylic acid by catalytic oxidation of propane or isobutane in the gaseous phase (i.e., catalytic reaction of propane or isobutane with molecular oxygen in the gaseous phase) and a process for producing (meth)acrylonitrile by catalytic ammoxidation of propane or isobutane in the gaseous phase (i.e., catalytic reaction of propane or isobutane with ammonia and molecular oxygen in the gaseous phase). Further, a number of proposals have been made with respect to catalysts for use in the above-mentioned processes for the catalytic oxidation and catalytic ammoxidation of propane or isobutane in the gaseous phase.

For example, as a catalyst for use in the above mentioned processes for the catalytic oxidation and catalytic ammoxidation of propane or isobutane in the gaseous phase, oxide catalysts containing molybdenum, vanadium, niobium and tellurium are known. Such oxide catalysts are disclosed in U.S. Pat. Nos. 5,049,692, 5,231,214 and 5,422,328, European Patent Publication No. 529 853 B1 and Unexamined Japanese Patent Application Laid-Open Specification Nos. 6-227819, 6-279351, 7-10801, 7-144132, 7-232071, 7-289907, 7-315842, 8-57319 and 8-141401.

As further examples of oxide catalysts for use in the above-mentioned processes for the catalytic oxidation and catalytic ammoxidation of propane or isobutane in the gaseous phase, an oxide catalyst containing tungsten, vanadium, tellurium and niobium, is disclosed in Unexamined Japanese Patent Application Laid-Open Specification No. 6-228073; oxide catalysts containing molybdenum, vanadium, antimony and niobium, are disclosed in European Patent Publication No. 767 164 A1 and Unexamined Japanese Patent Application Laid-Open Specification Nos. 5-213848, 9-316023 and 10-45664; and an oxide catalyst containing molybdenum, vanadium, bismuth and niobium, is disclosed in U.S. Pat. No. 4,760,159.

With respect to sources of niobium, the above-mentioned patent documents describe the use of $Nb_2O_5$, a niobic acid $(Nb_2O_5 \cdot nH_2O)$, $Nb_2(C_2O_4)_5$, niobium oxalate, niobium tartrate, ammonium niobium oxalate, ammonium niobium tartrate, $NbCl_3$, $NbCl_5$, $Nb(OEt)_5$, $Nb(O-n-Bu)_5$ and the like. However, heretofore, no study has ever been made with respect to the relationship between the composition of the niobium source and the catalytic activity of the niobium-containing oxide catalyst obtained.

For example, the above-mentioned U.S. Pat. No. 5,049,692 discloses the use of a niobium compound (called "ammonium niobium oxalate") as the niobium source; however, currently, the composition of the "ammonium niobium oxalate" is not known, and U.S. Pat. No. 5,049,692 has no description about the composition of the "ammonium niobium oxalate", such as a molar ratio of oxalic acid to niobium.

The above-mentioned U.S. Pat. No. 4,760,159 discloses the use of an aqueous slurry of $Nb_2O_5$; the above-mentioned Unexamined Japanese Patent Application Laid-Open Specification No. 9-316023 discloses the use of a solution of a niobic acid in a mixture of water and oxalic acid, wherein a large amount of oxalic acid is used (molar ratio of the oxalic acid to the niobium in the niobic acid: about 6.0 to 8.5); and the above-mentioned Unexamined Japanese Patent Application Laid-Open Specification No. 6-227819 discloses the use of a solution obtained by dissolving $Nb(O-n-Bu)_5$ in 1,4-butanediol. However, none of these patent documents describes the composition of the niobium source and the relationship between the composition of the niobium source and the catalytic activity of the obtained oxide catalyst.

The above-mentioned Unexamined Japanese Patent Application Laid-Open Specification No. 7-315842 teaches that niobium compounds, such as niobium oxalate, niobium tartrate, ammonium niobium oxalate and ammonium niobium tartrate, have high solubilities in water as well as in aqueous solvents containing alcohols, organic acids or inorganic acids, so that these niobium compounds can be handled with ease; however, this patent document also has no description about the composition (such as a molar ratio of oxalic acid to niobium) of each of the above-mentioned niobium compounds and the relationship between the composition of the niobium compound and the catalytic activity of the obtained oxide catalyst.

The conventional oxide catalysts produced using the above-mentioned conventional niobium sources do not have satisfactory catalytic activities. Therefore, by the use of such conventional oxide catalysts, it is impossible to produce (meth)acrylic acid or (meth)acrylonitrile in high yield. Particularly, when the above-mentioned oxidation or ammoxidation is per-formed in a fluidized bed reactor using a carrier-supported catalyst comprising any of the above-mentioned conventional oxide catalysts, the carrier is likely to adversely affect the reaction, thereby leading to a lowering of the yield of (meth)acrylic acid or (meth)acrylonitrile.

Further, the above-mentioned Unexamined Japanese Patent Application Laid-Open Specification No. 7-315842 teaches that a compound oxide catalyst (containing niobium) having high catalytic activity can be obtained by a method comprising: (1) mixing a niobium-containing aqueous solution with an aqueous solution containing compounds of active component elements of the oxide catalyst other than niobium to thereby obtain an aqueous compound solution; (2) removing the aqueous solvent from the aqueous compound solution by, for example, spray drying or freeze drying before the precipitation of the insoluble matters occurs, to thereby obtain a solid catalyst precursor; and (3) calcining the obtained solid catalyst precursor. However, there are only 10 minutes between the mixing in step (1) above and the occurrence of the precipitation. Therefore, the technique of this patent document is difficult to practice on a commercial scale.

Therefore, it has strongly been desired to develop an oxide catalyst which not only can be advantageously used for producing (meth)acrylic acid or (meth)acrylonitrile in high yield, but also can be efficiently produced on a commercial scale.

SUMMARY OF THE INVENTION

In this situation, the present inventors have made extensive and intensive studies with a view toward solving the above-mentioned problems accompanying the conventional niobium-containing oxide catalyst and developing a niobium-containing catalyst which not only can be advantageously used for producing (meth)acrylic acid or (meth) acrylonitrile in high yield, but also can be efficiently produced on a commercial scale. As a result, it has unexpectedly been found that, when a niobium-containing aqueous solution having a specific composition is used for producing an oxide catalyst comprising an oxide of a plurality of active component elements including niobium (wherein the production of the oxide catalyst is generally performed by a process comprising mixing a niobium-containing aqueous solution with an aqueous mixture or aqueous mixtures containing compounds of active component elements of the oxide catalyst other than niobium, to thereby provide an aqueous compound mixture, and drying the obtained aqueous compound mixture, followed by calcination), it becomes possible to produce efficiently an oxide catalyst which exhibits high catalytic activity, so that it can be advantageously used for producing (meth)acrylic acid or (meth) acrylonitrile in high yield. The above-mentioned niobium-containing aqueous solution having a specific composition comprises water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$. The present invention has been made, based on this novel finding.

Accordingly, it is a primary object of the present invention to provide a niobium-containing aqueous solution which, when used as a niobium source in the production of a niobium-containing oxide catalyst, enables the efficient production of a niobium-containing oxide catalyst which can be advantageously used for producing (meth)acrylic acid or (meth)acrylonitrile in high yield.

It is another object of the present invention to provide an oxide catalyst which not only can be efficiently produced by using the above-mentioned niobium-containing aqueous solution, but also can be advantageously used for producing (meth)acrylic acid or (meth)acrylonitrile in high yield.

The foregoing and other objects, features and advantages of the present invention will be apparent to those skilled in the art from the following detailed description and appended claims.

DETAILED DESCRIPTION OF THE INVENTION

In one aspect of the present invention, there is provided a niobium-containing aqueous solution for use in producing a niobium-containing oxide catalyst, wherein the niobium-containing oxide catalyst comprises an oxide of a plurality of active component elements including niobium and is for use in a catalytic oxidation or ammoxidation of propane or isobutane in the gaseous phase, and wherein the niobium-containing oxide catalyst is prepared by a process comprising mixing the niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination, the niobium-containing aqueous solution comprising water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$.

In another aspect of the present invention, there is provided an oxide catalyst for use in a catalytic oxidation or ammoxidation of propane or isobutane in the gaseous phase, comprising an oxide of a plurality of active component elements including niobium, wherein the niobium-containing oxide catalyst is prepared by a process comprising mixing a niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination, the niobium-containing aqueous solution comprising water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$.

For easy understanding of the present invention, the essential features and various embodiments of the present invention is enumerated below.

1. A niobium-containing aqueous solution for use in producing a niobium-containing oxide catalyst, wherein the niobium-containing oxide catalyst comprises an oxide of a plurality of active component elements including niobium and is for use in a catalytic oxidation or ammoxidation of propane or isobutane in the gaseous phase, and wherein the niobium-containing oxide catalyst is prepared by a process comprising mixing the niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination, the niobium-containing aqueous solution comprising water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$.

2. The niobium-containing aqueous solution according to item 1, wherein the molar ratio ($\alpha$) of the dicarboxylic acid to the niobium contained in the niobium compound satisfies the following relationship: $2 \leq (\alpha) \leq 4$, and the molar ratio ($\beta$) of the ammonia to the niobium contained in the niobium compound satisfies the following relationship: $0 \leq (\beta) \leq 1$.

3. The niobium-containing aqueous solution according to item 1 or 2, wherein the active component elements of the niobium-containing oxide catalyst are niobium, molybdenum, vanadium, and at least one element selected from the group consisting of tellurium and antimony.

4. The niobium-containing aqueous solution according to any one of items 1 to 3, which is prepared by a process comprising:
   (i) mixing water, a dicarboxylic acid and a niobium compound to thereby obtain a preliminary niobium-containing aqueous solution or a niobium-containing aqueous semisolution having suspended therein a part of the niobium compound;
   (ii) cooling the preliminary niobium-containing aqueous solution or niobium-containing aqueous semisolution to thereby precipitate a part of the dicarboxylic acid; and
   (iii) removing the precipitated dicarboxylic acid from the preliminary niobium-containing aqueous solution, or removing the precipitated dicarboxylic acid and the suspended niobium compound from the niobium-containing aqueous semisolution, thereby obtaining a niobium-containing aqueous solution.

5. The niobium-containing aqueous solution according to any one of items 1 to 3, which is prepared by a process comprising:
   (i) mixing water, a dicarboxylic acid and a niobium compound to thereby obtain a niobium-containing aqueous semisolution having suspended therein a part of the niobium compound; and
   (ii) removing the suspended niobium compound from the niobium-containing aqueous semisolution, thereby obtaining a niobium-containing aqueous solution.

6. The niobium-containing aqueous solution according to any one of items 1 to 3, which is prepared by a process comprising:
   (i) adding a niobium compound to an aqueous acidic solution to thereby obtain a niobium-containing aqueous acidic semisolution having suspended therein a part of the niobium compound;
   (ii) removing the suspended niobium compound from the niobium-containing aqueous acidic semisolution to thereby obtain a niobium-containing aqueous acidic solution;
   (iii) adding a basic compound to the niobium-containing aqueous acidic solution to precipitate the niobium in the form of a niobic acid;
   (iv) recovering the precipitated niobic acid; and
   (v) dissolving the niobic acid in a mixture of water and a dicarboxylic acid, thereby obtaining a niobium-containing aqueous solution.

7. The niobium-containing aqueous solution according to any one of items 1 to 3, which is prepared by a process comprising:
   (i) adding a niobium compound to an aqueous basic solution to thereby obtain a niobium-containing aqueous basic semisolution having suspended therein a part of the niobium compound;
   (ii) removing the suspended niobium compound from the niobium-containing aqueous basic semisolution to thereby obtain a niobium-containing aqueous basic solution;
   (iii) adding an acidic compound to the niobium-containing aqueous basic solution to precipitate the niobium in the form of a niobic acid;
   (iv) recovering the precipitated niobic acid; and
   (v) dissolving the niobic acid in a mixture of water and a dicarboxylic acid, thereby obtaining a niobium-containing aqueous solution.

8. The niobium-containing aqueous solution according to any one of items 4 to 7, wherein the niobium compound is at least one compound selected from the group consisting of a niobic acid and niobium hydrogenoxalate, and the dicarboxylic acid is oxalic acid.

9. A niobium-containing oxide catalyst for use in a catalytic oxidation or ammoxidation of propane or isobutane in the gaseous phase, comprising an oxide of a plurality of active component elements including niobium, wherein the niobium-containing oxide catalyst is prepared by a process comprising mixing a niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination, the niobium-containing aqueous solution comprising water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$.

10. The oxide catalyst according to item 9, wherein the active component elements are niobium, molybdenum, vanadium, and at least one element selected from the group consisting of tellurium and antimony.

11. The oxide catalyst according to item 9 or 10, which further comprises a silica carrier having supported thereon the oxide of a plurality of active component elements, wherein the silica carrier is present in an amount of from 20 to 70% by weight, based on the total weight of the oxide and the silica carrier.

12. A process for producing a niobium-containing oxide catalyst for use in a catalytic oxidation or ammoxidation of propane or isobutane in the gaseous phase, wherein the niobium-containing oxide catalyst comprises an oxide of a plurality of active component elements including niobium, the process comprising mixing a niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination, the niobium-containing aqueous solution comprising water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$.

13. The process according to item 12, wherein the active component elements are niobium, molybdenum, vanadium, and at least one element selected from the group consisting of tellurium and antimony.

14. The process according to item 12 or 13, wherein the aqueous compound mixture is provided so as to further contain a silica sol in an amount such that the oxide catalyst further comprises a silica carrier in an amount of from 20 to 70% by weight, based on the total amount of the oxide and the silica carrier, the silica carrier having supported thereon the oxide of a plurality of active component elements.

15. A process for producing acrylic acid or methacrylic acid from propane or isobutane by oxidation in the gaseous phase, comprising:

providing a niobium-containing oxide catalyst comprising an oxide of a plurality of active component elements including niobium, wherein the niobium-containing oxide catalyst is prepared by a process comprising mixing a niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination, the niobium-containing aqueous solution comprising water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$; and reacting propane or isobutane with molecular oxygen in the gaseous phase in the presence of the niobium-containing oxide catalyst.

16. The process according to item 15, wherein the active component elements of the niobium-containing oxide catalyst are niobium, molybdenum, vanadium, and at least one element selected from the group consisting of tellurium and antimony.

17. The process according to item 15 or 16, wherein the niobium-containing oxide catalyst further comprises a silica carrier having supported thereon the oxide of a plurality of active component elements, wherein the silica carrier is present in an amount of from 20 to 70% by weight, based on the total weight of the oxide and the silica carrier.

18. A process for producing acrylonitrile or methacrylonitrile from propane or isobutane by ammoxidation in the gaseous phase, comprising:

providing a niobium-containing oxide catalyst comprising an oxide of a plurality of active component elements including niobium, wherein the niobium-containing oxide catalyst is prepared by a process comprising mixing a niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination, the niobium-containing aqueous solution comprising water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$; and reacting propane or isobutane with ammonia and molecular oxygen in the gaseous phase in the presence of the niobium-containing oxide catalyst.

19. The process according to item 18, wherein the active component elements of the niobium-containing oxide catalyst are niobium, molybdenum, vanadium, and at least one element selected from the group consisting of tellurium and antimony.

20. The process according to item 18 or 19, wherein the niobium-containing oxide catalyst further comprises a silica carrier having supported thereon the oxide of a plurality of active component elements, wherein the silica carrier is present in an amount of from 20 to 70% by weight, based on the total weight of the oxide and the silica carrier.

Hereinbelow, the present invention will be described in more detail.

In one aspect of the present invention, there is provided a niobium-containing aqueous solution for use in producing a niobium-containing oxide catalyst, comprising water having dissolved therein a dicarboxylic acid, a niobium compound and optionally ammonia, wherein the molar ratio ($\alpha$) of the dicarboxylic acid to the niobium contained in the niobium compound satisfies the following relationship: $1 \leq (\alpha) \leq 4$, and the molar ratio ($\beta$) of the ammonia to the niobium contained in the niobium compound satisfies the following relationship: $0 \leq (\beta) \leq 2$.

The niobium-containing aqueous solution of the present invention can be advantageously used in producing a niobium-containing oxide catalyst, wherein the oxide catalyst comprises an oxide of a plurality of active component elements including niobium and is for use in a catalytic oxidation or ammoxidation of propane or isobutane in the gaseous phase, and wherein the niobium-containing oxide catalyst is prepared by a process comprising mixing the niobium-containing aqueous solution with an aqueous mixture or aqueous mixtures containing compounds of active component elements of the oxide catalyst other than niobium, to thereby provide an aqueous compound mixture, and drying the aqueous compound mixture, followed by calcination. The catalyst produced by using the niobium-containing aqueous solution of the present invention exhibits high catalytic activity, so that it can be advantageously used for producing (meth)acrylic acid or (meth)acrylonitrile in high yield.

Examples of dicarboxylic acids used in the niobium-containing aqueous solution of the present invention include oxalic acid, tartaric acid, malonic acid, succinic acid and phthalic acid. Of these, oxalic acid is preferred. The oxalic acid is generally available in the form of oxalic acid dihydrate or oxalic acid anhydride.

Examples of niobium compounds used in the niobium-containing aqueous solution of the present invention include a niobic acid, niobium hydrogenoxalate and oxotrioxalatoammoniumniobate $\{(NH_4)_3[NbO(C_2O_4)_3]\cdot 1.5H_2O\}$. Of these, a niobic acid and niobium hydrogenoxalate are preferred. The niobic acid is a hydrated compound represented by the following formula: $Nb_2O_5 \cdot nH_2O$, which is also known as "niobium hydroxide" or "niobium oxide hydrate".

In the niobium-containing aqueous solution of the present invention, the molar ratio ($\alpha$) of the dicarboxylic acid to the niobium contained in the niobium compound satisfies the relationship: $1 \leq (\alpha) \leq 4$, preferably $2 \leq (\alpha) \leq 4$, more preferably $2 \leq (\alpha) \leq 3.5$. When the dicarboxylic acid/niobium molar ratio ($\alpha$) of the niobium-containing aqueous solution is outside the above-mentioned range, a problem is caused such that an oxide catalyst prepared using the niobium-containing aqueous solution has disadvantageously low catalytic activity.

In the present invention, it is preferred that the concentration of the niobium compound (in terms of the niobium atom) in the niobium-containing aqueous solution is in the range of from 0.2 to 0.8 mol/kg of the niobium-containing aqueous solution.

The niobium-containing aqueous solution of the present invention may optionally contain ammonia [wherein the ammonia may be present either in the form of ammonia ($NH_3$) or in the form of an ammonium ion ($NH_4^+$)]; however, it is necessary that the molar ratio ($\beta$) of the ammonia to the niobium contained in the niobium compound be 2 or less. It is preferred that the molar ratio ($\beta$) is 1 or less. When the ammonia/niobium molar ratio ($\beta$) of the niobium-containing aqueous solution is more than 2, a problem is caused such that an oxide catalyst prepared using the niobium-containing aqueous solution has disadvantageously low catalytic activity.

When a niobium compound capable of generating ammonium ions, such as the above-mentioned oxotrioxalatoammoniumniobate, is used to produce the niobium-containing aqueous solution of the present invention, the resultant aqueous solution inevitably contains ammonia. In this case, it is necessary that the ammonia content of the niobium-containing aqueous solution be controlled by using a niobium compound incapable of generating ammonium ions in combination with the niobium compound capable of generating ammonium ions, so that the ammonia/niobium molar ratio ($\beta$) of the niobium-containing aqueous solution becomes 2 or less.

In the present invention, for obtaining a niobium-containing aqueous solution which can be advantageously used for producing an oxide catalyst having high catalytic activity, it is preferred that the niobium-containing aqueous solution contains no niobium compound undissolved and suspended therein. When the niobium-containing aqueous solution of the present invention contains suspended particles of niobium compound, a disadvantage is likely to be caused such that the catalytic activity of an oxide catalyst produced using the niobium-containing aqueous solution becomes lower. Therefore, even if the niobium-containing aqueous solution of the present invention contains suspended particles of niobium compound, it is preferred that the amount of the suspended particles of niobium compound is as small as possible. Specifically, the amount of the suspended particles of niobium compound is preferably 2% or less, more preferably 1% or less, most preferably 0.5% or less, in terms of the weight ratio (%) of the suspended niobium compound to the total of the dissolved niobium compound and the suspended niobium compound.

The weight of the suspended particles of niobium compound can be determined by, for example, the following method. A predetermined amount of the niobium-containing aqueous solution is subjected to a suction filtration using a filter paper (such as, "No. 101<135 mm>; quantity 100" manufactured and sold by TOYO ROSHI KAISHA Ltd., Japan), to thereby obtain a filtration residue. The obtained residue is dried overnight at 95° C., and calcined at 850° C. for 2 hours, to thereby isolate the niobium compound in the form of niobium oxide, and the weight of the obtained niobium oxide is measured.

The total weight of the dissolved niobium compound and the suspended niobium compound can be determined by, for example, the following method. A predetermined amount of the niobium-containing aqueous solution is added to a crucible and dried overnight at 95° C., followed by calcination at 850° C. for 2 hours, to thereby obtain the niobium compound in the form of niobium oxide, and the weight of the obtained niobium oxide is measured.

The method for producing the niobium-containing aqueous solution of the present invention is explained hereinbelow.

In the production of the niobium-containing aqueous solution of the present invention, when a niobium compound having high solubility as defined below is used, the niobium-containing aqueous solution of the present invention can be obtained simply by mixing water, a dicarboxylic acid and a niobium-containing compound while stirring, wherein the molar ratio of the dicarboxylic acid to the niobium contained in the niobium compound is adjusted so as to be in the range of from 1 to 4. The above-mentioned niobium compound having high solubility is defined as a niobium compound which can be completely dissolved in an aqueous solution of dicarboxylic acid when water, a dicarboxylic acid and a niobium compound are mixed, while stirring, under the following conditions:

(1) The temperature of mixing is from 50 to 100° C.;

(2) The molar ratio of the dicarboxylic acid to the niobium contained in the niobium compound is in the range of from 1 to 4; and (3) The niobium concentration of the mixture of water, the dicarboxylic acid and the niobium compound is in the range of from 0.2 to 0.8 mol/kg of the mixture.

However, most of commercially available niobium compounds cannot be completely dissolved in the aqueous solution of dicarboxylic acid under the above-mentioned conditions (1) to (3) (such niobium compounds are, hereinafter, referred to simply as "niobium compounds having low solubility"). In addition, with respect to commercially available niobic acid products, even in the case of the same type of niobic acid, different lots of niobic acid products have different solubilities in the aqueous solution of dicarboxylic acid.

When such a niobium compound having low solubility is employed to obtain the niobium-containing aqueous solution of the present invention, it is possible that a part of the niobium compound remains undissolved in the aqueous solution of dicarboxylic acid. However, even when such a niobium compound having low solubility is employed, the niobium-containing aqueous solution of the present invention can be easily prepared in accordance with any one of the below-described four methods (A) to (D). Hereinbelow, detailed explanation is made with respect to a preferred embodiment of each of methods (A) to (D).

Method (A) (cooling method):
This method (cooling method) comprises the steps of:
(i) mixing water, a dicarboxylic acid and a niobium compound to thereby obtain a preliminary niobium-containing aqueous solution or a niobium-containing aqueous semisolution having suspended therein a part of the niobium compound;
(ii) cooling the preliminary niobium-containing aqueous solution or niobium-containing aqueous semisolution to thereby precipitate a part of the dicarboxylic acid; and
(iii) removing the precipitated dicarboxylic acid from the preliminary niobium-containing aqueous solution, or removing the precipitated dicarboxylic acid and the suspended niobium compound from the niobium-containing aqueous semisolution,
thereby obtaining a niobium-containing aqueous solution.

In step (i) of method (A) (cooling method), water, a dicarboxylic acid and a niobium compound are mixed together to obtain a preliminary niobium-containing aqueous solution or a niobium-containing aqueous semisolution (the term "semisolution" means a certain form of the mixture of water, a dicarboxylic acid and a niobium compound, in which most of the niobium compound molecules are dissolved but a small amount of the niobium compound molecules remains undissolved).

With respect to the dicarboxylic acid used in method (A), oxalic acid is preferred.

With respect to the niobium compound used in method (A), a niobic acid and niobium hydrogenoxalate are preferred. These niobium compounds can be used individually or in combination.

For example, step (i) of method (A) can be performed by dissolving a dicarboxylic acid (such as oxalic acid) in water to thereby obtain an aqueous solution of dicarboxylic acid, and then mixing a niobium compound (such as a niobic acid or niobium hydrogenoxalate) with the aqueous solution of dicarboxylic acid at about 50° to about 100° C. so that the [dicarboxylic acid/Nb] molar ratio is preferably in the range of from 0.5 to 10, more preferably from 3 to 8. When the [dicarboxylic acid/Nb] molar ratio is more than 10, a large amount of the niobium compound can be dissolved in the aqueous solution of dicarboxylic acid; however, a disadvantage is likely to arise in that the amount of the dicarboxylic acid which is caused to precipitate by the cooling in the below-described step (ii) becomes too large, thus decreasing the utilization of the dicarboxylic acid. On the other hand, when the [dicarboxylic acid/Nb] molar ratio is less than 0.5, a disadvantage is likely to arise in that a large amount of the niobium compound remains undissolved and is suspended in the aqueous solution of dicarboxylic acid to form a semisolution, wherein the suspended niobium compound is removed from the semisolution in the below-described step (iii), thus decreasing the degree of utilization of the niobium compound.

Step (i) of method (A) can also be performed by dissolving niobium hydrogenoxalate in water to thereby obtain a preliminary niobium-containing aqueous solution or a niobium-containing aqueous semisolution.

The niobium concentration of the preliminary aqueous solution or aqueous semisolution obtained by step (i) of method (A) is preferably selected within the range of from 0.2 to 0.8 mol/kg of the solution or semisolution.

In step (ii) of method (A), the aqueous solution or aqueous semisolution obtained by step (i) above is cooled to thereby precipitate a part of the dicarboxylic acid.

The cooling method is not particularly limited. The cooling can be performed simply, for example, by means of ice, specifically by a method in which a vessel containing the solution or semisolution is placed on ice and allowed to cool, while stirring. By means of such cooling, a part of the dicarboxylic acid is precipitated.

In step (iii) of method (A), the precipitated dicarboxylic acid is removed from the preliminary niobium-containing aqueous solution, or the precipitated dicarboxylic acid and the suspended niobium compound are removed from the niobium-containing aqueous semisolution, to thereby obtain a niobium-containing aqueous solution.

The removal operation in step (iii) can be performed by a conventional method, for example, by decantation or filtration. The obtained niobium-containing aqueous solution can be stored at room temperature.

In the niobium-containing aqueous solution obtained by method (A) above, the molar ratio ($\alpha$) of the dicarboxylic acid to the niobium contained in the niobium compound satisfies the relationship: $2 \leq (\alpha) \leq 4$.

In the present invention, the molar ratio ($\alpha$) in the obtained niobium-containing aqueous solution is determined as follows. First, the niobium concentration of the niobium-containing aqueous solution is determined as follows. A sample having a predetermined weight is taken from the niobium-containing aqueous solution and subjected to drying, thereby obtaining a dried niobium compound. The obtained niobium compound is calcined at 5000 to 1,000° C. for 30 minutes or more in an atmosphere of air, to thereby obtain niobium oxide ($Nb_2O_5$), and the obtained niobium oxide is subjected to gravimetric analysis, thereby determining the molar amount of niobium in the original niobium-containing aqueous solution. Next, the concentration of the dicarboxylic acid in the niobium-containing aqueous solution is determined by a conventional method. For example, when oxalic acid is used as the dicarboxylic acid, the oxalic acid concentration of the niobium-containing aqueous solution can be determined by permanganate titration. Based on the obtained dicarboxylic acid concentration, the molar amount of the dicarboxylic acid in the niobium-containing aqueous solution is determined. The molar ratio ($\alpha$) is determined from the thus obtained molar amounts of the niobium and dicarboxylic acid in the niobium-containing aqueous solution.

It is preferred that the molar ratio ($\alpha$) satisfies the relationship: $2 \leq (\alpha) \leq 3.5$. If desired, a dicarboxylic acid or a niobium compound may be added to the niobium-containing aqueous solution so that the molar ratio ($\alpha$) falls within the above preferred range. As a supplementary niobium compound to be added for adjusting the molar ratio ($\alpha$), it is preferable to use a niobic acid which has high solubility in an aqueous solution of dicarboxylic acid. As examples of such a highly soluble niobic acid, there can be mentioned a niobic acid obtained by step (iv) of the below-described method (C) and a niobic acid obtained by step (iv) of the below-described method (D).

Method (B) (insoluble Nb compound removal method):
This method (insoluble Nb compound removal method) comprises the steps of:
(i) mixing water, a dicarboxylic acid and a niobium compound to thereby obtain a niobium-containing aqueous semisolution having suspended therein a part of the niobium compound; and
(ii) removing the suspended niobium compound from the niobium-containing aqueous semisolution,
thereby obtaining a niobium-containing aqueous solution.

In step (i) of method (B), water, a dicarboxylic acid and a niobium compound are mixed together to obtain a niobium-containing aqueous semisolution.

With respect to the dicarboxylic acid used in method (B), oxalic acid is preferred.

With respect to the niobium compound used in method (B), a niobic acid is preferred.

For example, step (i) of method (B) can be performed by dissolving a dicarboxylic acid (such as oxalic acid) in water to thereby obtain an aqueous solution of dicarboxylic acid, and then mixing a niobium compound (such as a niobic acid) with the aqueous solution of dicarboxylic acid at about 50° to about 100° C. so that the [dicarboxylic acid/Nb] molar ratio is in the range of from about 1 to about 4.

The niobium concentration of the aqueous semisolution obtained by step (i) of method (B) is preferably selected within the range of from 0.2 to 0.8 mol/kg of the aqueous semisolution.

In step (ii) of method (B), the suspended niobium compound is removed from the niobium-containing aqueous semisolution obtained by step (i), to thereby obtain a niobium-containing aqueous solution.

The removal of the suspended niobium compound in step (ii) can be performed, for example, by filtration, such as suction filtration or filtration under pressure. The amount of the suspended niobium compound removed from the aqueous semisolution is generally 10% by weight or less, based on the weight of the niobium compound used instep (i) for obtaining the aqueous semisolution.

In the niobium-containing aqueous solution obtained by method (B), the molar ratio ($\alpha$) of the dicarboxylic acid to the niobium contained in the niobium compound satisfies the relationship: $1 \leq (\alpha) \leq 4$. It is preferred that the molar ratio ($\alpha$) satisfies the relationship: $2 \leq (\alpha) \leq 4$, more advantageously $2 \leq (\alpha) \leq 3.5$. If desired, a dicarboxylic acid or a niobium compound may be added to the niobium-containing aqueous solution so that the molar ratio ($\alpha$) falls within the above preferred range. As a supplementary niobium compound to be added for adjusting the molar ratio ($\alpha$), it is preferable to use a niobic acid which has high solubility in an aqueous solution of dicarboxylic acid. As examples of such a highly soluble niobic acid, there can be mentioned a niobic acid obtained by step (iv) of the below-described method (C) and a niobic acid obtained by step (iv) of the below-described method (D).

Method (C) (acidic solution-basic compound method):

This method (acidic solution-basic compound method) comprises the steps of:

(i) adding a niobium compound to an aqueous acidic solution to thereby obtain a niobium-containing aqueous acidic semisolution having suspended therein a part of the niobium compound;

(ii) removing the suspended niobium compound from the niobium-containing aqueous acidic semisolution to thereby obtain a niobium-containing aqueous acidic solution;

(iii) adding a basic compound to the niobium-containing aqueous acidic solution to precipitate the niobium in the form of a niobic acid;

(iv) recovering the precipitated niobic acid; and (v) dissolving the niobic acid in a mixture of water and a dicarboxylic acid, thereby obtaining a niobium-containing aqueous solution.

In step (i) of method (C), a niobium compound is added to an aqueous acidic solution to thereby obtain a niobium-containing aqueous acidic semisolution.

Examples of aqueous acidic solutions include aqueous solutions of oxalic acid, tartaric acid, acetic acid, hydrochloric acid, hydrofluoric acid, nitric acid, sulfuric acid and phosphoric acid. Among these aqueous acidic solutions, an aqueous solution of oxalic acid and an aqueous solution of tartaric acid are preferred.

With respect to the niobium compound used in method (C), a niobic acid is preferred.

For example, step (i) of method (C) can be performed by adding a niobium compound (such as a niobic acid) to an aqueous acidic solution (such as an aqueous solution of oxalic acid or tartaric acid) at about 50° to about 100° C. in an amount such that the [aqueous acidic solution-derived acid/Nb] molar ratio is in the range of from 4 to 8. The resultant aqueous acidic semisolution has suspended therein only a small part of the niobium compound.

The niobium concentration of the aqueous acidic semisolution obtained by step (i) of method (C) is preferably selected within the range of from 0.2 to 0.8 mol/kg of the aqueous acidic semisolution.

In step (ii) of method (C), the suspended niobium compound is removed from the niobium-containing aqueous acidic semisolution obtained by step (i) above to thereby obtain a niobium-containing aqueous acidic solution. The removal of the suspended niobium compound in step (ii) can be performed by a conventional method, for example, by decantation, filtration or centrifugation.

In step (iii) of method (C), a basic compound is added to the niobium-containing aqueous acidic solution obtained by step (ii) to precipitate the niobium in the form of a niobic acid.

Examples of basic compounds used instep (iii) of method (C) include ammonia, hydroxides of alkali metals and hydroxides of alkaline earth metals. Among these compounds, ammonia is preferred.

For example, step (iii) of method (C) can be performed by adding a basic compound (such as ammonia) to the aqueous acidic solution obtained by step (ii) above, while stirring, in an amount such that the pH of the resultant mixture is in the range of from 2 to 12, preferably from 5 to 10, to thereby precipitate the niobium in the form of a niobic acid.

In step (iv) of method (C), the niobic acid precipitated in step (iii) above is recovered. The recovery of the precipitated niobic acid can be performed by a conventional method, for example, by decantation, filtration or centrifugation.

It is preferred that the recovered niobic acid is thoroughly washed, and then dried. The drying can be performed in an atmosphere of air, more preferably under a stream of air or in vacuo, at a temperature of from 50° to 130° C. It is also preferred that the drying of the niobic acid is conducted under conditions wherein the niobic acid does not experience local heating to any large extent. The resultant dried niobic acid has an Nb content such that, when the dried niobic acid is calcined at 500° to 1,000° C. for 30 minutes or more in an atmosphere of air, $Nb_2O_5$ is obtained in an amount of 10 to 84% by weight, preferably 20 to 82% by weight, based on the weight of the original dried niobic acid before calcination.

In step (v) of method (C), the niobic acid obtained by step (iv) above is dissolved in a mixture of water and a dicarboxylic acid to thereby obtain a niobium-containing aqueous solution of the present invention.

As the dicarboxylic acid used instep (v) of method (C), oxalic acid is preferred.

In the niobium-containing aqueous solution obtained by method (C), the molar ratio ($\alpha$) of the dicarboxylic acid to the niobium contained in the niobium compound satisfies the relationship: $1 \leq (\alpha) \leq 4$, preferably $2 \leq (\alpha) \leq 4$, more preferably $2 \leq (\alpha) \leq 3.5$.

Method (D) (basic solution-acidic compound method):

This method (basic solution-acidic compound method) comprises the steps of:

(i) adding a niobium compound to an aqueous basic solution to thereby obtain a niobium-containing aqueous basic semisolution having suspended therein a part of the niobium compound;

(ii) removing the suspended niobium compound from the niobium-containing aqueous basic semisolution to thereby obtain a niobium-containing aqueous basic solution;

(iii) adding an acidic compound to the niobium-containing aqueous basic solution to precipitate the niobium in the form of a niobic acid;

(iv) recovering the precipitated niobic acid; and (v) dissolving the niobic acid in a mixture of water and a dicarboxylic acid, thereby obtaining a niobium-containing aqueous solution.

In step (i) of method (C), a niobium compound is added to an aqueous basic solution to thereby obtain a niobium-containing aqueous basic semisolution.

Examples of aqueous basic solutions include aqueous solutions of alkali metal hydroxides and aqueous ammonia. Among these aqueous basic solutions, an aqueous solution of potassium hydroxide and an aqueous solution of sodium hydroxide are preferred.

With respect to the niobium compound used in method (D), a niobic acid is preferred.

For example, step (i) of method (D) can be performed by charging a niobium compound (such as a niobic acid) into an autoclave together with an aqueous basic solution (such as an aqueous solution of potassium hydroxide or sodium hydroxide) and then heating the resultant mixture at 100° C. or more. The resultant aqueous basic semisolution has suspended therein only a small part of the niobium compound.

The concentration of the base in the aqueous basic semisolution obtained by step (i) of method (D) can be selected within the range of from 1 to 10 mol/kg of the aqueous basic semisolution. The niobium concentration of the aqueous basic semisolution obtained by step (i) of method (D) is preferably selected within the range of from 0.2 to 0.8 mol/kg of the aqueous basic semisolution.

In step (ii) of method (D), the suspended niobium compound is removed from the niobium-containing aqueous basic semisolution obtained by step (i) above to thereby obtain a niobium-containing aqueous basic solution. The removal of the suspended niobium compound in step (ii) can be performed by a conventional method, such as decantation, filtration or centrifugation.

In step (iii) of method (D), an acidic compound is added to the niobium-containing aqueous basic solution obtained by step (ii) to precipitate the niobium in the form of a niobic acid.

Examples of acidic compounds used in step (iii) of method (D) include nitric acid, hydrochloric acid, sulfuric acid, phosphoric acid, oxalic acid, tartaric acid and acetic acid. Among these acids, nitric acid is preferred.

For example, step (iii) of method (D) can be performed by adding an acidic compound (such as nitric acid) to the aqueous basic solution obtained by step (ii) above, while stirring, in an amount such that the pH of the resultant mixture is in the range of from 12 to 6, preferably from 10 to 7, to thereby precipitate the niobium in the form of a niobic acid.

In step (iv) of method (D), the precipitated niobic acid formed by step (iii) above is recovered. The recovery of the precipitated niobic acid can be performed by a conventional method, for example by decantation, filtration or centrifugation.

It is preferred that the recovered niobic acid is thoroughly washed, and then dried. The drying can be performed in an atmosphere of air, more preferably under a stream of air or in vacuo, at a temperature of from 50° to 130° C. It is also preferred that the drying of the niobic acid is conducted under conditions wherein the niobic acid does not experience local heating to any large extent. The resultant dried niobic acid has an Nb content such that, when the dried niobic acid is calcined at 500° to 1,000° C. for 30 minutes or more in an atmosphere of air, $Nb_2O_5$ is obtained in an amount of 10 to 84% by weight, preferably 20 to 82% by weight, based on the weight of the original dried niobic acid before calcination.

In step (v) of method (D), the niobic acid obtained by step (iv) above is dissolved in a mixture of water and a dicarboxylic acid to thereby obtain a niobium-containing aqueous solution of the present invention.

As the dicarboxylic acid used in step (v) of method (D), oxalic acid is preferred.

In the niobium-containing aqueous solution obtained by method (D), the molar ratio ($\alpha$) of the dicarboxylic acid to the niobium contained in the niobium compound satisfies the relationship: $1 \leq (\alpha) \leq 4$, preferably $2 \leq (\alpha) \leq 4$, more preferably $2 \leq (\alpha) \leq 3.5$.

In another aspect of the present invention, there is provided a niobium-containing oxide catalyst for use in a catalytic oxidation or ammoxidation of propane or isobutane in the gaseous phase, comprising an oxide of a plurality of active component elements including niobium (i.e., a compound oxide). The oxide catalyst of the present invention is prepared by a process comprising mixing the niobium-containing aqueous solution of the present invention with an aqueous mixture or aqueous mixtures containing compounds of active component elements of the oxide catalyst other than niobium, to thereby provide an aqueous compound mixture, and drying the aqueous compound mixture, followed by calcination.

In the present invention, it is preferred that the oxide catalyst comprises a compound oxide of niobium, molybdenum, vanadium, and at least one element selected from the group consisting of tellurium and antimony.

With respect to the sources of active component elements other than niobium, there is no particular limitation as long as the source contains a desired element. Specifically, it is preferred that ammonium heptamolybdate is used as a source of molybdenum; ammonium metavanadate is used as a source of vanadium; telluric acid is used as a source of tellurium; and an antimony oxide is used as a source of antimony.

In addition to those active component elements, the oxide catalyst may optionally contain at least one component element selected from the group consisting of the following elements: W, Cr, Ta, Ti, Zr, Hf, Mn, Re, Fe, Ru, Co, Rh, Ni, Pd, Pt, Cu, Ag, Zn, B, Al, Ga, In, Ge, Sn, Pb, P, Bi, rare earth elements, and alkaline earth metals. Examples of sources of these elements include a nitrate, an oxalate, an acetate, a hydroxide, an oxide, an ammonium salt and a carbonate of the above-mentioned at least one component element.

As a specific example of a composition of the oxide catalyst of the present invention, there can be mentioned a composition represented by the following formula:

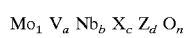

wherein:

X is at least one element selected from the group consisting of Te and Sb;

Z is at least one element selected from the group consisting of W, Cr, Ta, Ti, Zr, Hf, Mn, Re, Fe, Ru, Co, Rh, Ni, Pd, Pt, Cu, Ag, Zn, B, Al, Ga, In, Ge, Sn, Pb, P, Bi, rare earth elements, and alkaline earth metals; and a, b, c, d and n are, respectively, the atomic ratios of vanadium, nioblum, X, Z and oxygen, relative to molybdenum, wherein $0.1 \leq a \leq 1.0$, preferably $0.2 \leq a \leq 0.6$;

$0.01 \leq b \leq 1.0$, preferably $0.05 \leq b \leq 0.5$;

$0.01 \leq c \leq 1.0$, preferably $0.05 \leq c \leq 0.5$;

$0 \leq d \leq 1.0$, preferably $0 \leq d \leq 0.1$, and n is a number determined by the valence requirements of the other elements present.

The oxide catalyst of the present invention may further comprise a carrier having supported thereon the oxide of a plurality of active component elements. Examples of carriers used in the present invention include silica, alumina, titania, magnesia and zirconia. Of the above-mentioned carriers, silica is preferred. When silica is used as a carrier, a preferred source of silica is a silica sol. Examples of silica sols include a silica sol stabilized with alkali metal ions and a silica sol stabilized with ammonium ions. Of these, the silica sol stabilized with ammonium ions is preferred.

When the oxide catalyst of the present invention is in a silica-supported form, the oxide catalyst does not suffer a lowering of the catalytic activity, differing from the conventional silica-supported oxide catalysts for use in a catalytic oxidation or ammoxidation of propane or isobutane in the gaseous phase.

The amount of the carrier is preferably from 20 to 70% by weight, more preferably from 20 to 60% by weight, based on the total weight of the oxide and the carrier.

For producing the oxide catalyst of the present invention, which is supported by a carrier, source of a carrier (such as silica) may be added to at least one member selected from the group consisting of the above-defined niobium-containing aqueous solution, the above-defined aqueous mixture or mixtures containing compounds of active component elements of the oxide catalyst other than niobium, and the above-defined aqueous compound mixture in the process for producing the oxide catalyst.

The oxide catalyst of the present invention can be produced by the above mentioned process using the niobium-containing aqueous solution of the present invention. More specifically, the oxide catalyst of the present invention can be prepared by a process comprising the steps of (1) mixing the niobium-containing aqueous solution of the present invention with an aqueous mixture or aqueous mixtures containing compounds of active component elements of the oxide catalyst other than niobium, to thereby provide an aqueous compound mixture, (2) drying the aqueous compound mixture obtained in step (1) above to obtain a dried catalyst precursor, and (3) calcining the dried catalyst precursor obtained in step (2) above.

Hereinbelow, explanation is made with respect to a preferred embodiment of the above-mentioned process for producing the oxide catalyst of the present invention, which comprises steps (1), (2) and (3) above.

In step (1), an aqueous compound mixture is prepared. First, an aqueous mixture is prepared by dissolving ammonium heptamolybdate, ammonium metavanadate and telluric acid in water (this aqueous mixture is designated "aqueous mixture A"). Alternatively, when antimony is used as a component element, an aqueous mixture is first prepared by a method in which an antimony trioxide powder is dispersed in an aqueous solution of ammonium metavanadate, thereby obtaining a dispersion, and the obtained dispersion is heated under reflux conditions to thereby obtain a solution or slurry, and then, ammonium heptamolybdate and, optionally, telluric acid are added to the obtained solution or slurry to obtain an aqueous mixture (this aqueous mixture is designated "aqueous mixture A'").

In addition, when the above-mentioned at least one optional element is used as an active component element, an aqueous mixture is prepared by dissolving in water a source (e.g., a nitrate, an oxalate, an acetate, a hydroxide, an oxide, an ammonium salt or a carbonate) of the at least one optional element (this aqueous mixture is designated "aqueous mixture B").

To aqueous mixture A or A' are successively added the niobium-containing aqueous solution of the present invention and (optionally) aqueous mixture B in accordance with the desired composition for the catalyst, to thereby obtain an aqueous compound mixture.

When the oxide catalyst of the present invention further comprises a silica carrier having supported thereon the oxide of a plurality of active components, the aqueous compound mixture further contains a silica sol. The addition of a silica sol can be made at any time during the above preparation operation for the aqueous compound mixture, which comprises preparing aqueous mixture A or A', the niobium-containing aqueous solution of the present invention and optionally aqueous mixture B, and mixing these liquids together.

The aqueous compound mixture prepared in the above manner can be obtained in the form of a solution, but is generally obtained in the form of a slurry.

In step (2), the aqueous compound mixture obtained in step (1) above is subjected to spray drying. The spray drying of the mixture can be generally conducted by centrifugation, two-phase flow nozzle method or high pressure nozzle method to obtain a dried particulate catalyst precursor. In this instance, it is preferred to use air which has been heated by an electric heater, steam or the like, as a heat source for drying. It is preferred that the temperature of the spray dryer at an entrance to the dryer section thereof is from 150° to 300° C. Spray drying can be performed in an alternative handy way, for example, by spraying the aqueous compound mixture onto a steel plate which has been heated to a temperature of 100° to 300° C.

In step (3), the dried particulate catalyst precursor obtained in step (2) above is calcined to thereby obtain an oxide catalyst. The dried particulate catalyst precursor is calcined in an atmosphere of an inert gas, such as nitrogen gas, argon gas or helium gas, which is substantially free of oxygen, preferably under a stream of an inert gas, at a temperature of 500° to 700° C., preferably 550° to 650° C. for 0.5 to 20 hours, preferably 1 to 8 hours.

For the calcination, a kiln, such as a rotary kiln, a tunnel kiln, a muffle kiln or a fluidized firing kiln can be used.

Prior to the calcination in step (3), the dried catalyst precursor obtained in step (2) above may be heat-treated in an atmosphere of air or under a stream of air at a temperature of 200° to 400° C. for 1 to 5 hours.

(Meth)acrylic acid or (meth)acrylonitrile can be produced by the gaseous phase oxidation or the gaseous phase ammoxidation of propane or isobutane in the presence of the niobium-containing oxide catalyst of the present invention.

The process of the present invention for producing (meth) acrylic acid or (meth)acrylonitrile can be conducted in a conventional reactor, such as a fixed-bed reactor, a fluidized-bed reactor or a moving-bed reactor. Of these reactors, a fluidized-bed reactor is preferred from the viewpoint of ease in removal of the heat generated during the oxidation or ammoxidation. The reaction mode employed in the process of the present invention may be either a one-pass mode or a recycling mode.

Propane or isobutane and ammonia used in the process of the present invention need not be of very high purity but may be of a commercial grade.

Examples of sources of molecular oxygen include air, an oxygen-rich air and pure oxygen. Further, such a source of molecular oxygen may be diluted with helium, argon, nitrogen, carbon dioxide, steam or the like.

In the present invention, the catalytic oxidation reaction of propane or isobutane in the gaseous phase can be conducted under the following conditions. The molar ratio of molecular oxygen to propane or isobutane used for the oxidation is generally in the range of from 1:0.5 to 1:10, preferably from 1:1 to 1:5. The oxidation temperature is generally in the range of from 300° to 500° C., preferably from 350° to 450° C. The oxidation pressure is generally in the range of from 0.5 to 5 atm., preferably from 1 to 3 atm. The time of contact (contact time) between the gaseous feedstocks and the catalyst is generally in the range of from 0.1 to 10 sec·g/cc, preferably from 0.5 to 5 sec·g/cc.

In the process of the present invention, the contact time during the catalytic oxidation of propane or isobutane or during the catalytic ammoxidation of propane or isobutane is determined according to the following formula:

$$\text{Contact time (sec} \cdot \text{g/cc)} = (W/F) \times \frac{273}{(273+T)}$$

wherein:
W represents the weight (g) of the catalyst contained in the reactor;
F represents the flow rate (Ncc/sec) of the gaseous feedstocks [Ncc means cc as measured under the normal temperature and pressure conditions (0° C., 1 atm)]; and
T represents the reaction temperature (° C.).

In the present invention, the catalytic ammoxidation of propane or isobutane in the gaseous phase can be conducted under the following conditions. The [propane or isobutane-:ammonia:molecular oxygen] molar ratio is generally in the range of from 1:0.3 to 1.5:0.5 to 10, preferably from 1:0.8 to 1.2:1 to 5. The ammoxidation temperature is generally in the range of from 350° to 500° C., preferably from 380° to 470° C. The ammoxidation pressure is generally in the range of from 0.5 to 5 atm., preferably from 1 to 3 atm. The time of contact (contact time) between the gaseous feedstocks and the catalyst is generally in the range of from 0.1 to 10 sec·g/cc, preferably from 0.5 to 5 sec·g/cc.

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, an ammoxidation of propane and an oxidation of propane were conducted to produce acrylonitrile and acrylic acid, respectively.

The results of the ammoxidation were evaluated in terms of the conversion (%) of propane, the selectivity (%) for acrylonitrile and the yield (%) of acrylonitrile, which are, respectively, defined as follows:

$$\text{Conversion (\%) of propane} = \frac{\text{mole of propane reacted}}{\text{mole of propane fed}} \times 100$$

$$\text{Selectivity (\%) for acrylonitrile} = \frac{\text{mole of acrylonitrile formed}}{\text{mole of propane reacted}} \times 100$$

$$\text{Yield of acrylonitrile (\%)} = \frac{\text{mole of acrylonitrile formed}}{\text{mole of propane fed}} \times 100$$

The results of the oxidation were evaluated in terms of the conversion (%) of propane, the selectivity (%) for acrylic acid and the yield (%) of acrylic acid, which are, respectively, defined as follows:

$$\text{Conversion (\%) of propane} = \frac{\text{mole of propane reacted}}{\text{mole of propane fed}} \times 100$$

$$\text{Selectivity (\%) for acrylic acid} = \frac{\text{mole of acrylic acid formed}}{\text{mole of propane reacted}} \times 100$$

$$\text{Yield of acrylic acid (\%)} = \frac{\text{mole of acrylic acid formed}}{\text{mole of propane fed}} \times 100$$

EXAMPLE 1

(Preparation of a niobium-containing aqueous solution)

To 170 g of water were added 17.64 g of niobic acid (A) (manufactured and sold by Soekawa Chemical Co., Ltd., Japan) ($Nb_2O_5$ content: 76.6% by weight) and 34.60 g of oxalic acid ($H_2C_2O_4 \cdot 2H_2O$), while stirring at about 60° C., to thereby obtain a niobium-containing aqueous solution (E-1) having an oxalic acid/Nb molar ratio of 2.7.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared as follows.

To 720 g of water were added 164.31 g of ammonium heptamolybdate [$(NH_4)_6Mo_7O_{24} \cdot 4H_2O$], 36.05 g of ammonium metavanadate ($NH_4VO_3$) and 47.15 g of telluric acid ($H_6TeO_6$), while stirring at 60° C., to thereby obtain an aqueous solution.

To the obtained aqueous solution was added 300 g of a silica sol having a $SiO_2$ content of 30% by weight, while stirring, followed by cooling to 30° C. and subsequent addition of the niobium-containing aqueous solution (E-1), to thereby obtain an aqueous compound mixture.

The obtained aqueous compound mixture was subjected to a spray drying by means of a centrifugation type spray-drying apparatus under conditions such that the entrance and exit temperatures of the dryer of the spray-drying apparatus were 240° C. and 145° C., respectively, to thereby obtain a dried particulate catalyst precursor.

The obtained catalyst precursor was heat-treated in the air at 275° C. for 2 hours to obtain a compound oxide. 85 g of the obtained compound oxide was charged into a SUS tube (diameter: 1 inch) and calcined at 600° C. for 2 hours under a flow of nitrogen gas at a flow rate of 150 Ncc/min (Ncc means cc as measured under the normal temperature and pressure conditions, namely, at 0° C. under 1 atm.), to thereby obtain a silica-supported, niobium-containing oxide catalyst.

(Ammoxidation of propane)

45 g of the oxide catalyst obtained above was charged into a Vycor glass fluidized-bed reaction tube having an inner diameter of 25 mm. A gaseous mixture having a molar ratio of propane:ammonia:oxygen:helium of 1:1.2:3:12 was fed into the reaction tube from the lower portion thereof at a flow rate of 5.83 Ncc/sec, to thereby effect an ammoxidation of propane to produce acrylonitrile. The reaction temperature was 430° C., and the reaction pressure was atmospheric pressure. The time of contact (contact time) between the oxide catalyst and the gaseous mixture of the feedstocks was 3.0 sec·g/cc. The results of the ammoxidation are shown in Table 1, together with the composition of the niobium-containing aqueous solution used for producing the catalyst.

EXAMPLE 2

(Preparation of a niobium-containing aqueous solution)

Preparation of a niobium-containing aqueous solution was performed in substantially the same manner as in Example 1, except that oxalic acid ($H_2C_2O_4 \cdot 2H_2O$) was used in an amount of 38.45 g, to thereby obtain a niobium-containing aqueous solution (E-2) having an oxalic acid/Nb molar ratio of 3.0.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared in substantially the same manner as in Example 1, except that the niobium-containing aqueous solution (E-2) was used instead of the niobium-containing aqueous solution (E-1).

(Ammoxidation of propane)

The ammoxidation of propane was performed in substantially the same manner as in Example 1, except that the oxide catalyst prepared above was used instead of the oxide catalyst prepared in Example 1. The results of the ammoxidation of propane are shown in Table 1, together with the composition of the niobium-containing aqueous solution used for producing the catalyst.

EXAMPLE 3

(Preparation of a niobium-containing aqueous solution)

To 160 g of water were added 17.64 g of niobic acid (A) ($Nb_2O_5$ content: 76.6% by weight), 38.45 g of oxalic acid ($H_2C_2O_4 \cdot 2H_2O$) and 6.9 g of aqueous ammonia ($NH_3$ content: 25% by weight), while stirring at about 60° C., to thereby obtain a niobium-containing aqueous solution (E-3) having an oxalic acid/Nb molar ratio of 3.0 and an ammonia/Nb molar ratio of 1.0.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared in substantially the same manner as in Example 1, except that the niobium-containing aqueous solution (E-3) was used instead of the niobium-containing aqueous solution (E-1).

(Ammoxidation of propane)

The ammoxidation of propane was performed in substantially the same manner as in Example 1, except that the oxide catalyst prepared above was used instead of the oxide catalyst prepared in Example 1. The results of the ammoxidation of propane are shown in Table 1, together with the composition of the niobium-containing aqueous solution used for producing the catalyst.

COMPARATIVE EXAMPLE 1

(Preparation of a niobium-containing aqueous solution)

Preparation of a niobium-containing aqueous solution was performed in substantially the same manner as in Example 3, except that water and aqueous ammonia ($NH_3$ content: 25% by weight) were, respectively, used in amounts of 150 g and 16.6 g, to thereby obtain a niobium-containing aqueous solution (C-1) having an oxalic acid/Nb molar ratio of 3.0 and an ammonia/Nb molar ratio of 2.4.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared in substantially the same manner as in Example 1, except that the niobium-containing aqueous solution (C-1) was used instead of the niobium-containing aqueous solution (E-1).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 1, together with the composition of the niobium-containing aqueous solution used for producing the catalyst.

EXAMPLE 4

(Preparation of a niobium-containing aqueous solution)

Preparation of a niobium-containing aqueous solution was performed in substantially the same manner as in Example 1, except that water and oxalic acid ($H_2C_2O_4 \cdot 2H_2O$) were, respectively, used in amounts of 160 g and 44.85 g, to thereby obtain a niobium-containing aqueous solution (E-4) having an oxalic acid/Nb molar ratio of 3.5.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared in substantially the same manner as in Example 1, except that the niobium-containing aqueous solution (E-4) was used instead of the niobium-containing aqueous solution (E-1).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 1, together with the composition of the nioblum-containing aqueous solution used for producing the catalyst.

EXAMPLE 5

(Preparation of a niobium-containing aqueous solution)

Preparation of a niobium-containing aqueous solution was performed in substantially the same manner as in Example 4, except that oxalic acid ($H_2C_2O_4 \cdot 2H_2O$) was used in an amount of 51.26 g, to thereby obtain a niobium-containing aqueous solution (E-5) having an oxalic acid/Nb molar ratio of 4.0.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared in substantially the same manner as in Example 1, except that the niobium-containing aqueous solution (E-5) was used instead of the niobium-containing aqueous solution (E-1).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 1, together with the composition of the niobium-containing aqueous solution used for producing the catalyst.

COMPARATIVE EXAMPLE 2

(Preparation of a niobium-containing aqueous solution)

Preparation of a niobium-containing aqueous solution was performed in substantially the same manner as in Example 1, except that water and oxalic acid ($H_2C_2O_4 \cdot 2H_2O$) were, respectively, used in amounts of 110 g and 96.11 g, to thereby obtain a niobium-containing aqueous solution (C-2) having an oxalic acid/Nb molar ratio of 7.5.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared in substantially the same manner as in Example 1, except that the niobium-containing aqueous solution (C-2) was used instead of the niobium-containing aqueous solution (E-1).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 1, together with the composition of the niobium-containing aqueous solution used for producing the catalyst.

EXAMPLE 6

(Preparation of a niobium-containing aqueous solution)

To 120 g of water were added 12.60 g of niobic acid (A) ($Nb_2O_5$ content: 76.6% by weight) and 27.46 g of oxalic acid ($H_2C_2O_4 \cdot 2H_2O$), while stirring at about 60° C., to thereby obtain a niobium-containing aqueous solution (E-6) having an oxalic acid/Nb molar ratio of 3.0.

(Preparation of a niobium-containing oxide catalyst)

A niobium-containing oxide catalyst comprising a silica carrier having supported thereon a compound oxide, wherein the silica carrier is present in an amount of 50% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared as follows.

To 510 g of water were added 117.36 g of ammonium heptamolybdate [$(NH_4)_6Mo_7O_{24} \cdot 4H_2O$], 25.75 g of ammonium metavanadate ($NH_4VO_3$) and 33.68 g of telluric acid ($H_6TeO_6$), while stirring at 60° C., to thereby obtain an aqueous solution.

To the obtained aqueous solution was added 500 g of a silica sol having a $SiO_2$ content of 30% by weight, while stirring, followed by cooling to 30° C. and subsequent addition of the niobium-containing aqueous solution (E-6), to thereby obtain an aqueous compound mixture.

The obtained aqueous compound mixture was subjected to spray drying, heat-treatment and calcination in substantially the same manner as in Example 1, to thereby obtain a silica-supported, niobium-containing oxide catalyst.

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 1, together with the composition of the niobium-containing aqueous solution used for producing the catalyst.

COMPARATIVE EXAMPLE 3

(Preparation of a niobium-containing aqueous solution)

Preparation of a niobium-containing aqueous solution was performed in substantially the same manner as in Example 6, except that water and oxalic acid ($H_2C_2O_4 \cdot 2H_2O$) were, respectively, used in amounts of 80 g and 68.65 g, to thereby obtain a niobium-containing aqueous solution (C-3) having an oxalic acid/Nb molar ratio of 7.5.

(Preparation of a niobium-containing oxide catalyst)

A niobium-containing oxide catalyst comprising a silica carrier having supported thereon a compound oxide, wherein the silica carrier is present in an amount of 50% by weight in terms of $SiO_2$, based on the total weight of the compound oxide and the silica carrier, and wherein the compound oxide is represented by the formula: $Mo_1V_{0.33}Nb_{0.11}Te_{0.22}O_n$, was prepared in substantially the same manner as in Example 6, except that the niobium-containing aqueous solution (C-3) was used instead of the niobium-containing aqueous solution (E-6).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 1, together with the composition of the niobium-containing aqueous solution used for producing the catalyst.

EXAMPLE 7

(Preparation of a niobium-containing aqueous solution)

To 250 g of water were added 25.20 g of niobic acid (A) ($Nb_2O_5$ content: 76.6 t by weight) and 45.77 g of oxalic acid ($H_2C_2O_4 \cdot 2H_2O$), while stirring at about 60° C., to thereby obtain a niobium-containing aqueous solution (E-7) having an oxalic acid/Nb molar ratio of 2.5.

(Preparation of a niobium-containing oxide catalyst: $Mo_1V_{0.33}Nb_{0.11}Te_{0.22}O_n$)

To 1,030 g of water were added 234.72 g of ammonium heptamolybdate [$(NH_4)_6Mo_7O_{24} \cdot 4H_2O$], 51.49 g of ammonium metavanadate ($NH_4VO_3$) and 67.35 g of telluric acid ($H_6TeO_6$), while stirring at 60° C., to thereby obtain an aqueous solution thereof.

The obtained aqueous solution was cooled to 30° C., and then, the niobium-containing aqueous solution (E-7) was added to the aqueous solution to thereby obtain an aqueous compound mixture.

The obtained aqueous compound mixture was subjected to spray drying, heat-treatment and calcination in substantially the same manner as in Example 1, to thereby obtain a niobium-containing oxide catalyst.
(Ammoxidation of propane)

1 g of the oxide catalyst obtained above was charged into a fixed-bed reaction tube having an inner diameter of 10 mm. A gaseous mixture having a [propane:ammonia:oxygen:helium] molar ratio of 1:1.2:3:12 was fed into the reaction tube at a flow rate of 0.388 Ncc/sec, to thereby effect an ammoxidation of propane to produce acrylonitrile. The reaction temperature was 430° C., and the reaction pressure was atmospheric pressure. The contact time was 1.0 sec.g/cc. The results of the ammoxidation are shown in Table 1, together with the composition of the niobium-containing aqueous solution used for producing the catalyst.

EXAMPLE 8

(Preparation of a niobium-containing aqueous solution)

To 240 g of water were added 25.20 g of niobic acid (A) ($Nb_2O_5$ content: 76.6% by weight), 45.77 g of oxalic acid ($H_2C_2O_4 \cdot 2H_2O$) and 9.9 g of aqueous ammonia ($NH_3$ content: 25% by weight), while stirring at about 60° C., to thereby obtain a niobium-containing aqueous solution (E-8) having an oxalic acid/Nb molar ratio of 2.5 and an ammonia/Nb molar ratio of 1.0.
(Preparation of a niobium-containing oxide catalyst: $Mo_1V_{0.33}Nb_{0.11}Te_{0.22}O_n$)

Preparation of a niobium-containing oxide catalyst was performed in substantially the same manner as in Example 7, except that the niobium-containing aqueous solution (E-8) was used instead of the niobium-containing aqueous solution (E-7).
(Ammoxidation of propane)

The ammoxidation of propane was performed in substantially the same manner as in Example 7, except that the oxide catalyst prepared above was used instead of the oxide catalyst prepared in Example 7. The results of the ammoxidation of propane are shown in Table 1, together with the composition of the niobium-containing aqueous solution used for producing the catalyst.

COMPARATIVE EXAMPLE 4

(Preparation of a niobium-containing aqueous solution)

Preparation of a niobium-containing aqueous solution was performed in substantially the same manner as in Example 7, except that water and oxalic acid ($H_2C_2O_4 \cdot 2H_2O$) were, respectively, used in amounts of 160 g and 137.31 g, to thereby obtain a niobium-containing aqueous solution (C-4) having an oxalic acid/Nb molar ratio of 7.5.
(Preparation of a niobium-containing oxide catalyst: $Mo_1V_{0.33}Nb_{0.11}Te_{0.22}O_n$)

A niobium-containing oxide catalyst was prepared in substantially the same manner as in Example 7, except that the niobium-containing aqueous solution (C-4) was used instead of the niobium-containing aqueous solution (E-7).
(Ammoxidation of propane)

The ammoxidation of propane was performed in substantially the same manner as in Example 7, except that the oxide catalyst prepared above was used instead of the oxide catalyst prepared in Example 7. The results of the ammoxidation of propane are shown in Table 1, together with the composition of the niobium-containing aqueous solution used for producing the catalyst.

COMPARATIVE EXAMPLE 5

(Preparation of a niobium-containing aqueous solution)

Preparation of a niobium-containing aqueous solution was performed in substantially the same manner as in Example 8, except that water and aqueous ammonia ($NH_3$ content: 25% by weight) were, respectively, used in amounts of 110 g and 49.5 g, to thereby obtain a niobium-containing aqueous solution (C-5) having an oxalic acid/Nb molar ratio of 7.5 and an ammonia/Nb molar ratio of 5.0.
(Preparation of a niobium-containing oxide catalyst: $Mo_1V_{0.33}Nb_{0.11}Te_{0.22}O_n$)

A niobium-containing oxide catalyst was prepared in substantially the same manner as in Example 7, except that the niobium-containing aqueous solution (C-5) was used instead of the niobium-containing aqueous solution (E-7).
(Ammoxidation of propane)

The ammoxidation of propane was performed in substantially the same manner as in Example 7, except that the oxide catalyst prepared above was used instead of the oxide catalyst prepared in Example 7. The results of the ammoxidation of propane are shown in Table 1, together with the composition of the niobium-containing aqueous solution used for producing the catalyst.

TABLE 1

| | Niobium-containing aqueous solution | | | | $SiO_2$ content of catalyst[*1] (wt. %) | Ammoxidation of propane to produce acrylonitrile | | |
|---|---|---|---|---|---|---|---|---|
| | Niobium compound | Dicarboxylic acid | Oxalic acid/Nb (molar ratio) | Ammonia/Nb (molar ratio) | | Type of reactor[*2] | Conversion (%) | Selectivity (%) | Yield (%) |
| Ex. 1 | Niobic acid (A) | Oxalic acid | 2.7 | 0 | 30 | Fluidized-bed reactor | 84.0 | 57.0 | 47.9 |
| Ex. 2 | Niobic acid (A) | Oxalic acid | 3.0 | 0 | 30 | Fluidized-bed reactor | 85.2 | 60.9 | 51.9 |
| Ex. 3 | Niobic acid (A) | Ammoniacal oxalic acid | 3.0 | 1 | 30 | Fluidized-bed reactor | 85.0 | 59.0 | 50.2 |
| Comp. Ex. 1 | Niobic acid (A) | Ammoniacal oxalic acid | 3.0 | 2.4 | 30 | Fluidized-bed reactor | 72.8 | 46.6 | 33.9 |
| Ex. 4 | Niobic acid (A) | Oxalic acid | 3.5 | 0 | 30 | Fluidized-bed reactor | 84.9 | 60.1 | 51.0 |
| Ex. 5 | Niobic acid (A) | Oxalic acid | 4.0 | 0 | 30 | Fluidized-bed reactor | 79.7 | 60.0 | 47.8 |
| Comp. | Niobic | Oxalic acid | 7.5 | 0 | 30 | Fluidized- | 74.1 | 52.8 | 39.1 |

TABLE 1-continued

| | Niobium-containing aqueous solution | | | | SiO$_2$ content of catalyst*1) (wt. %) | Ammoxidation of propane to produce acrylonitrile | | |
|---|---|---|---|---|---|---|---|---|---|
| | Niobium compound | Dicarboxylic acid | Oxalic acid/Nb (molar ratio) | Ammonia/Nb (molar ratio) | | Type of reactor*2) | Conversion (%) | Selectivity (%) | Yield (%) |
| Ex. 2 | acid (A) | | | | | bed reactor | | | |
| Ex. 6 | Niobic acid (A) | Oxalic acid | 3.0 | 0 | 50 | Fluidized-bed reactor | 77.0 | 58.4 | 45.0 |
| Comp. Ex. 3 | Niobic acid (A) | Oxalic acid | 7.5 | 0 | 50 | Fluidized-bed reactor | 60.6 | 41.3 | 25.0 |
| Ex. 7 | Niobic acid (A) | Oxalic acid | 2.5 | 0 | 0 | Fixed-bed reactor | 88.1 | 60.3 | 53.1 |
| Ex. 8 | Niobic acid (A) | Ammoniacal oxalic acid | 2.5 | 1 | 0 | Fixed-bed reactor | 84.2 | 60.2 | 50.7 |
| Comp. Ex. 4 | Niobic acid (A) | Oxalic acid | 7.5 | 0 | 0 | Fixed-bed reactor | 73.9 | 62.1 | 45.9 |
| Comp. Ex. 5 | Niobic acid (A) | Oxalic acid | 7.5 | 5 | 0 | Fixed-bed reactor | 80.0 | 58.0 | 46.4 |

Notes
*1)Catalyst: Mo$_1$V$_{0.33}$Nb$_{0.11}$Te$_{0.22}$O$_n$/SiO$_2$
*2)Reaction conditions for ammoxidation using fluidized-bed rector (inner diameter: 25 mm): temperature = 430° C.; pressure = atmospheric pressure; contact time = 3.0 sec · g/cc; [propane:ammonia:oxygen:helium] molar ratio = 1:1.2:3:12
Reaction conditions for ammoxidation using fixed-bed rector (inner diameter: 10 mm): temperature = 430° C.; pressure = atmospheric pressure; contact time = 1.0 sec · g/cc; [propane:ammonia:oxygen:helium] molar ratio = 1:1.2:3:12

EXAMPLE 9
(Oxidation of propane)

2.0 g of the oxide catalyst prepared in Example 7 was charged into a fixed-bed reaction tube having an inner diameter of 10 mm. A flow (0.300 Ncc/sec) of a gaseous mixture having a [propane:oxygen:helium] molar ratio of 1:3.2:12.1 and a flow (0.257 Ncc/sec) of steam were combined together and then supplied to the reaction tube at the reaction temperature (380° C.) and under the reaction pressure (atmospheric pressure), to thereby effect an oxidation of the propane to produce acrylic acid. The contact time was 1.5 sec·g/cc. The results of the oxidation are shown in Table 2, together with the composition of the niobium-containing aqueous solution used for producing the catalyst.

COMPARATIVE EXAMPLE 6
(Oxidation of propane)

The oxidation of propane was performed in substantially the same manner as in Example 9, except that the oxide catalyst prepared in Comparative Example 4 was used instead of the oxide catalyst prepared in Example 7. The results of the oxidation are shown in Table 2, together with the composition of the niobium-containing aqueous solution used for producing the catalyst.

EXAMPLE 10
(Preparation of a niobium-containing aqueous solution)

To 125 g of water were added 12.76 g of niobic acid (A) (Nb$_2$O$_5$ content: 76.6% by weight) and 23.19 g of oxalic acid (H$_2$C$_2$H$_4$·2H$_2$O), while stirring at about 60° C., to thereby obtain a niobium-containing aqueous solution (E-10) having an oxalic acid/Nb molar ratio of 2.5.
(Preparation of a niobium-containing oxide catalyst: Mo$_1$V$_{0.33}$Nb$_{0.05}$Sb$_{0.16}$O$_n$)

To 1,150 g of water was added 57.37 g of ammonium metavanadate (NH$_4$VO$_3$), while stirring at 60° C., to thereby obtain an aqueous solution thereof. To the obtained aqueous solution was added 34.66 g of antimony trioxide (Sb$_2$O$_3$) powder, thereby obtaining a dispersion. The obtained dispersion was heated at 95° to 100° C. under reflux conditions for 10 hours while stirring, thereby obtaining a solution. 261.58 g of ammonium heptamolybdate [(NH$_4$)$_6$Mo$_7$O$_{24}$·4H$_2$O] was dissolved in the obtained solution at 60° C., and then, cooled to 10° C., thereby obtaining an aqueous solution.

To the obtained aqueous solution was added the niobium-containing aqueous solution (E-10) to thereby obtain an aqueous compound mixture.

The obtained aqueous compound mixture was subjected to a spray drying by means of a centrifugation type spray-drying apparatus under conditions such that the entrance and exit temperatures of the dryer of the spray-drying apparatus were 240° C. and 145° C., respectively, to thereby obtain a dried particulate catalyst precursor.

The obtained catalyst precursor was heated-treated in the air at 325° C. for 1 hour to thereby obtain a compound oxide. 85 g of the obtained compound oxide was charged into a SUS tube (diameter: 1 inch) and calcined at 600° C. for 2 hours under a flow of nitrogen gas at a flow rate of 150 Ncc/min, to thereby obtain a niobium-containing oxide catalyst.
(Oxidation of propane)

2.0 g of the oxide catalyst obtained above was charged into a fixed-bed reaction tube having an inner diameter of 10 mm. A flow (0.225 Ncc/sec) of a gaseous mixture having a [propane:oxygen:helium] molar ratio of 1:3.2:12.1 and a flow (0.193 Ncc/sec) of steam were combined together and supplied to the reaction tube at the reaction temperature (380° C.) and under the reaction pressure (atmospheric pressure), to thereby effect an oxidation of the propane to produce acrylic acid. The contact time was 2.0 sec·g/cc. The results of the oxidation are shown in Table 2, together with the composition of the niobium-containing aqueous solution used for producing the catalyst.

COMPARATIVE EXAMPLE 7
(Preparation of a niobium-containing aqueous solution)

Preparation of a niobium-containing aqueous solution was performed in substantially the same manner as in Example 10, except that water and oxalic acid (H$_2$C$_2$H$_4$·2H$_2$O) were, respectively, used in amounts of 80 g and 69.55 g, to thereby obtain a niobium-containing aqueous solution (C-7) having an oxalic acid/Nb molar ratio of 7.5.
(Preparation of a niobium-containing oxide catalyst: Mo$_1$V$_{0.33}$Nb$_{0.05}$Sb$^{0.16}$O$_n$)

A niobium-containing oxide catalyst was prepared in substantially the same manner as in Example 10, except that the niobium-containing aqueous solution (C-7) was used instead of the niobium-containing aqueous solution (E-10).
(Oxidation of propane)

The oxidation of propane was performed in substantially the same manner as in Example 10, except that the oxide catalyst prepared above was used instead of the oxide catalyst prepared in Example 10. The results of the oxidation are shown in Table 2, together with the composition of the niobium-containing aqueous solution used for producing the catalyst.

C. That is, the titration was conducted in accordance with the following reaction formula:

$$2KMnO_4+3H_2SO_4+5H_2C_2O_4 \rightarrow K_2SO_4+2MnSO_4+10CO_2+8H_2O.$$

An occurrence of a change in the color of the test solution in accordance with the progress of titration was examined. That is, the point at which the test solution was caused to assume a very light pink color due to the $KMnO_4$ and from which the test solution continued to have the very light pink color for 30 seconds or more, is defined as an end point of

TABLE 2

| | Niobium-containing aqueous solution | | | | | Oxidation of propane to produce acrylic acid | | | | |
|---|---|---|---|---|---|---|---|---|---|---|
| | Niobium compound | Dicarboxylic acid | Oxalic acid/Nb (molar ratio) | Ammonia/Nb (molar ratio) | Catalyst | Type of reactor*) | Contact time (sec · g/cc) | Conversion (%) | Selectivity (%) | Yield (%) |
| Ex. 9 | Niobic acid (A) | Oxalic acid | 2.5 | 0 | $Mo_1V_{0.33}Nb_{0.11}Te_{0.22}O_n$ | Fixed-bed reactor | 1.5 | 80.0 | 59.9 | 47.9 |
| Com. Ex. 6 | Niobic acid (A) | Oxalic acid | 7.5 | 0 | $Mo_1V_{0.33}Nb_{0.11}Te_{0.22}O_n$ | Fixed-bed reactor | 1.5 | 71.3 | 52.6 | 37.5 |
| Ex. 10 | Niobic acid (A) | Oxalic acid | 2.5 | 0 | $Mo_1V_{0.33}Nb_{0.05}Sb_{0.16}O_n$ | Fixed-bed reactor | 2.0 | 63.2 | 48.1 | 30.4 |
| Com. Ex. 7 | Niobic acid (A) | Oxalic acid | 7.5 | 0 | $Mo_1V_{0.33}Nb_{0.05}Sb_{0.16}O_n$ | Fixed-bed reactor | 2.0 | 39.3 | 35.2 | 13.8 |

Notes:
*)Reaction conditions for oxidation using fixed-bed rector (inner diameter: 10 mm): temperature = 380° C.; pressure = atmospheric pressure; [propane:oxygen:helium:steam] molar ratio = 1:3.2:12.1:14

EXAMPLE 11

[Preparation of a niobium-containing aqueous solution by Method (A) (cooling method)]

To 6,562 g of water were added 664.0 g of niobium acid (B) ("NIOBIA HY" manufactured and sold by COMPANHIA BRASILEIRA DE METALURGIA E MINERAGA, Brazil) ($Nb_2O_5$ content: 80% by weight) and 2,774.0 g of oxalic acid ($H_2C_2O_4.2H_2O$), and the resultant mixture was stirred at 95° C. for 1 hour, to thereby obtain a preliminary niobium-containing aqueous solution having an oxalic acid/Nb molar ratio of 5.5.

The obtained preliminary niobium-containing aqueous solution was cooled with ice, while stirring, to thereby precipitate a part of the oxalic acid.

While maintaining the temperature of the aqueous solution at about 2° C., the precipitated oxalic acid in the solution was removed from the aqueous solution by suction filtration, to thereby obtain a niobium-containing aqueous solution (E-11) having an oxalic acid/Nb molar ratio of 2.6. The oxalic acid/Nb molar ratio was determined by the following method.

First, the niobium concentration of the aqueous solution (E-11) was determined as follows. A 10 g sample solution was accurately taken from the aqueous solution (E-11) and charged into a crucible. The sample solution was dried overnight at 95° C., followed by calcination at 600° C. for 1 hour, thereby obtaining 0.625 g of $Nb_2O_5$. As a result, it was found that the niobium concentration of the aqueous solution (E-11) was 0.47 mol/kg of the aqueous solution.

Next, the oxalic acid concentration of the aqueous solution (E-11) was determined as follows. To a 300 ml glass beaker was added 3 g of the aqueous solution (E-11), followed by addition of 200 ml of water having a temperature of about 80° C. and 10 ml of sulfuric acid solution (volume ratio of concentrated sulfuric acid to water=1/1), to thereby obtain a test solution.

The obtained test solution was subjected to titration using 1/4 N $KMnO_4$ solution, while stirring the test solution at 70° C. From the amount of 1/4 N $KMnO_4$ solution consumed, the oxalic acid concentration of the aqueous solution (E-11) was calculated using the above reaction formula. As a result, it was found that the oxalic acid concentration of the niobium-containing aqueous solution was 1.22 mol/kg of the aqueous solution.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.32}Nb_{0.12}Te_{0.22}O_n$, was prepared as follows.

To 2,300 g of water were added 546.7 g of ammonium heptamolybdate [$(NH_4)_6Mo_7O_{24}.4H_2O$], 116.3 g of ammonium metavanadate ($NH_4VO_3$) and 156.9 g of telluric acid ($H_6TeO_6$), while stirring at 60° C., followed by cooling to 30° C., to thereby obtain an aqueous solution. To the obtained aqueous solution were added 785.0 g of the niobium-containing aqueous solution (E-11) and 1,000 g of a silica sol having a $SiO_2$ content of 30% by weight, to thereby obtain an aqueous compound mixture.

The obtained aqueous compound mixture was subjected to spray drying, heat-treatment and calcination in substantially the same manner as in Example 1, to thereby obtain a silica-supported, niobium-containing oxide catalyst.

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 3, together with the composition of the niobium-containing aqueous solution used for producing the catalyst.

EXAMPLE 12

[Preparation of a niobium-containing aqueous solution by Method (A) (cooling method)]

A part of the niobium-containing aqueous solution (E-11) obtained in Example 11 (having an oxalic acid/Nb molar ratio of 2.6) was taken and placed in a beaker. Oxalic acid ($H_2C_2O_4.2H_2O$) was added thereto and dissolved therein while stirring at 60° C., followed by cooling to 30° C., to thereby obtain a niobium-containing aqueous solution (E-12) having an oxalic acid/Nb molar ratio of 3.0. The niobium concentration of the aqueous solution determined in accordance with the method described in Example 11 was 0.46 mol/kg of the aqueous solution.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.32}Nb_{0.12}Te_{0.22}O_n$, was prepared in substantially the same manner as in Example 11 except that 802.1 g of the niobium-containing aqueous solution (E-12) was used instead of 785.0 g of the niobium-containing aqueous solution (E-11).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 3, together with the composition of the niobium-containing aqueous solution used for producing the catalyst.

EXAMPLE 13

[Preparation of a niobium-containing aqueous solution by Method (A) (cooling method)]

To 1,000 g of water was added 917.0 g of niobium hydrogenoxalate [$Nb(HC_2O_4)_5$] (manufactured and sold by Soekawa Chemical Co., Ltd., Japan) ($Nb_2O_5$ content: 14.9% by weight), and the resultant mixture was stirred at 95° C. for 1 hour, to thereby obtain a preliminary niobium-containing aqueous solution. The oxalic acid/Nb molar ratio of the aqueous solution was 5.2, as determined in accordance with the method described in Example 11.

The obtained aqueous solution was cooled with ice while stirring, to thereby precipitate a part of the oxalic acid.

While maintaining the temperature of the aqueous solution at about 2° C., the precipitated oxalic acid in the solution was removed by suction filtration, thereby obtaining a niobium-containing aqueous solution. The niobium concentration and oxalic acid concentration of the obtained aqueous solution were determined in accordance with the method described in Example 11. As a result, it was found that the niobium concentration and oxalic acid concentration of the obtained aqueous solution were 0.66 mol/kg of the aqueous solution and 1.58 mol/kg of the aqueous solution, respectively. Therefore, the oxalic acid/Nb molar ratio of the aqueous solution was 2.4.

559.1 g of the niobium-containing aqueous solution was placed in a beaker. 220 g of water and 28.0 g of oxalic acid ($H_2C_2O_4.2H_2O$) were added thereto while stirring at 60° C., followed by cooling to 30° C., to thereby obtain a niobium-containing solution (E-13) having an oxalic acid/Nb molar ratio of 3.0.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.32}Nb_{0.12}Te_{0.22}O_n$, was prepared in substantially the same manner as in Example 11, except that a whole amount of the niobium-containing aqueous solution (E-13) obtained above was used instead of 785.0 g of the niobium-containing aqueous solution (E-11).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 3, together with the composition of the niobium-containing aqueous solution used for producing the catalyst.

COMPARATIVE EXAMPLE 8

(Preparation of a niobium-containing aqueous solution)

To 600 g of water were added 61.3 g of niobic acid (B) ($Nb_2O_5$ content: 80% by weight) and 255.9 g of oxalic acid ($H_2C_2O_4.2H_2O$), and the resultant mixture was stirred at 95° C. for 1 hour, to thereby obtain a niobium-containing aqueous solution (C-8) having an oxalic acid/Nb molar ratio of 5.5.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.32}Nb_{0.12}Te_{0.22}O_n$, was prepared in substantially the same manner as in Example 11, except that a whole amount of the niobium-containing aqueous solution (C-8) obtained above was used instead of 785.0 g of the niobium-containing aqueous solution (E-11).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 3, together with the composition of the niobium-containing aqueous solution used for producing the catalyst.

EXAMPLE 14

[Preparation of a niobium-containing aqueous solution by Method (A) (cooling method)]

To 782 g of water were added 66.4 g of niobic acid (B) ($Nb_2O_5$ content: 80.0% by weight) and 151.3 g of oxalic acid ($H_2C_2O_4.2H_2O$), and the resultant mixture was stirred at 95° C. for 1 hour, to thereby obtain an aqueous semisolution having an oxalic acid/Nb molar ratio of 3.0.

The obtained aqueous semisolution was cooled with ice while stirring, to thereby precipitate a part of the oxalic acid.

While maintaining the temperature of the aqueous semisolution at about 2° C., the precipitated oxalic acid and the suspended niobic acid were removed from the aqueous semisolution by suction filtration, to thereby obtain a niobium-containing aqueous solution (E-14). The niobium concentration and oxalic acid concentration of the obtained aqueous solution (E-14) were determined in accordance with the method described in Example 11. As a result, it was found that the niobium concentration and oxalic acid concentration of the obtained aqueous solution (E-14) were 0.41 mol/kg of the aqueous solution and 1.15 mol/kg of the aqueous solution, respectively. Therefore, the oxalic acid/Nb molar ratio of the aqueous solution (E-14) was 2.8.
(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.32}Nb_{0.12}Te_{0.22}O_n$, was prepared in substantially the same manner as in Example 11, except that 899.9 g of the niobium-containing aqueous solution (E-14) obtained above was used instead of 785.0 g of the niobium-containing aqueous solution (E-11).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 3, together with the composition of the niobium-containing aqueous solution used for producing the catalyst.

EXAMPLE 15
[Preparation of a niobium-containing aqueous solution by Method (A) (cooling method)]

To 4,084 g of water were added 664.0 g of niobic acid (B) ($Nb_2O_5$ content: 80% by weight) and 252.0 g of oxalic acid ($H_2C_2O_4.2H_2O$), and the resultant mixture was stirred at 95° C. for 1 hour, to thereby obtain a niobium-containing aqueous semisolution having an oxalic acid/Nb molar ratio of 0.5.

The obtained aqueous semisolution was cooled with ice while stirring, to thereby precipitate a part of the oxalic acid.

While maintaining the temperature of the aqueous semi-solution at about 2° C., the precipitated oxalic acid and the suspended niobic acid were removed from the semisolution by suction filtration, thereby obtaining a niobium-containing aqueous solution. The niobium concentration and oxalic acid concentration of the obtained aqueous solution were determined in accordance with the method described in Example 11. As a result, it was found that the niobium concentration and oxalic acid concentration of the obtained aqueous solution were 0.16 mol/kg of the aqueous solution and 0.35 mol/kg of the aqueous solution, respectively. Therefore, the oxalic acid/Nb molar ratio of the aqueous solution was 2.2.

A part of the niobium-containing aqueous solution was taken and placed in a beaker. Oxalic acid ($H_2C_2O_4.2H_2O$) was added thereto and dissolved therein while stirring at 60° C., followed by cooling to 30° C., to thereby obtain a niobium-containing aqueous solution (E-15) having an oxalic acid/Nb molar ratio of 3.0. The niobium concentration of the niobium-containing aqueous solution (E-15) determined in accordance with the method described in Example 11 was 0.158 mol/kg of the aqueous solution.

(Preparation of a niobium-containing oxide catalyst)

A niobium-containing oxide catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula: $Mo_1V_{0.32}Nb_{0.12}Te_{0.22}O_n$, was prepared in substantially the same manner as in Example 11, except that 2335.2 g of the niobium-containing aqueous solution (E-15) was used instead of 785.0 g of the niobium-containing aqueous solution (E-11).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 3, together with the composition of the niobium-containing aqueous solution used for producing the catalyst.

EXAMPLE 16
[Preparation of a niobium-containing aqueous solution by Method (A) (cooling method)]

Preparation of a niobium-containing aqueous solution was performed in substantially the same manner as in Example 12 to thereby obtain a niobium-containing aqueous solution (E-16) having an oxalic acid/Nb molar ratio of 3.0. The niobium concentration of the aqueous solution as determined in accordance with the method described in Example 11 was 0.46 mol/kg of the aqueous solution.

(Preparation of a niobium-containing oxide catalyst)

A niobium-containing oxide catalyst comprising a silica carrier having supported thereon a compound oxide, wherein the silica carrier is present in an amount of 50% by weight in terms of $SiO_2$, based on the total weight of the compound oxide and the silica carrier, and wherein the compound oxide is represented by the formula: $Mo_1V_{0.32}Nb_{0.12}Te_{0.22}O_n$, was prepared as follows.

To 1,600 g of water were added 390.5 g of ammonium heptamolybdate [$(NH_4)6Mo_7O_{24}.4H_2O$], 83.1 g of ammonium metavanadate ($NH_4VO_3$) and 112.0 g of telluric acid ($H_6TeO_6$), while stirring at 60° C., followed by cooling to 30° C., to thereby obtain an aqueous solution. 572.9 g of the niobium-containing aqueous solution (E-16) and 1,667 g of a silica sol (having an $SiO_2$ content of 30% by weight) were added to the aqueous solution while stirring, thereby obtaining an aqueous compound mixture.

The obtained aqueous compound mixture was subjected to spray drying, heat-treatment and calcination in substantially the same manner as in Example 1, to thereby obtain a silica-supported, niobium-containing oxide catalyst.

(Ammoxidation of propane)

The ammoxidation of propane was performed in substantially the same manner as in Example 1, except that the oxide catalyst prepared above was used instead of the oxide catalyst obtained in Example 1. The results of the ammoxidation are shown in Table 3, together with the composition of the niobium-containing aqueous solution used for producing the catalyst.

COMPARATIVE EXAMPLE 9
(Preparation of a niobium-containing aqueous solution)

To 440 g of water were added 43.8 g of niobic acid (B) ($Nb_2O_5$ content: 80.0% by weight) and 182.8 g of oxalic acid ($H_2C_2O_4.2H_2O$), and the resultant mixture was stirred at 95° C. for 1 hour, to thereby obtain a niobium-containing aqueous solution (C-9) having an oxalic acid/Nb molar ratio of 5.5.

(Preparation of a niobium-containing oxide catalyst)

A niobium-containing oxide catalyst comprising a silica carrier having supported thereon a compound oxide, wherein the silica carrier is present in an amount of 50% by weight in terms of $SiO_2$, based on the total weight of the compound oxide and the silica carrier, and wherein the compound oxide is represented by the formula: $Mo_1V_{0.32}Nb_{0.12}Te_{0.22}O_n$, was prepared in substantially the same manner as in Example 16, except that a whole amount of the above-obtained niobium-containing aqueous solution (C-9) was used instead of 572.9 g of the niobium-containing aqueous solution (E-16).

(Ammoxidation of propane)

The ammoxidation of propane was performed in substantially the same manner as in Example 1, except that the oxide catalyst prepared above was used instead of the oxide catalyst prepared in Example 1. The results of the ammoxidation are shown in Table 3, together with the composition of the niobium-containing aqueous solution used for producing the catalyst.

EXAMPLE 17

(Preparation of a niobium-containing oxide catalyst: $Mo_1V_{0.32}Nb_{0.12}Te_{0.22}O_n$)

To 1,650 g of water were added 390.5 g of ammonium heptamolybdate [$(NH_4)6Mo_7O_{24}\cdot 4H_2O$], 83.1 g of ammonium metavanadate ($NH_4VO_3$) and 112.0 g of telluric acid ($H_6TeO_6$), while stirring at 60° C., followed by cooling to 30° C., to thereby obtain an aqueous solution. 560.7 g of the niobium-containing aqueous solution (E-11) obtained in Example 11 was added to the aqueous solution while stirring, to thereby obtain an aqueous compound mixture.

The obtained aqueous compound mixture was subjected to spray drying, heat-treatment and calcination in substantially the same manner as in Example 1, to thereby obtain a niobium-containing oxide catalyst.

(Ammoxidation of propane)

The ammoxidation of propane was performed in substantially in the same manner as in Example 7, except that the oxide catalyst prepared above was used instead of the oxide catalyst prepared in Example 7. The results of the ammoxidation are shown in Table 3, together with the composition of the niobium-containing aqueous solution used for producing the catalyst.

EXAMPLE 18

[Preparation of a niobium-containing aqueous solution by Method (A) (cooling method)]

To 510 g of water was added 195.70 g of oxalic acid ($H_2C_2O_4\cdot 2H_2O$), while stirring at about 70° C., to thereby obtain an oxalic acid solution. To the obtained oxalic acid solution was added 50.0 g of niobic acid (C) (manufactured and sold by Mitsuwakagaku Kabushikikaisha, Japan) ($Nb_2O_5$ content: 75.0% by weight), and the resultant mixture was stirred at about 70° C. for 1 hour, followed by cooling to about 30° C., to thereby obtain an niobium-containing aqueous semisolution having an oxalic acid/Nb molar ratio of 5.5.

The obtained aqueous semisolution was cooled with ice while stirring, to thereby precipitate a part of the oxalic acid.

While maintaining the temperature of the aqueous semisolution at about 2° C., the precipitated oxalic acid and suspended niobic acid were removed from the aqueous semisolution by suction filtration using a filter paper ("No. 101<135 mm>; quantity 100" manufactured and sold by TOYO ROSHI KAISHA Ltd., Japan), to thereby obtain a niobium-containing aqueous solution (E-18).

The niobium concentration and the oxalic acid concentration of the obtained aqueous solution were determined in accordance with the method described in Example 11. As a result, it was found that the niobium concentration and the oxalic acid concentration of the obtained aqueous solution were 0.46 mol/kg of the aqueous solution and 1.21 mol/kg of the aqueous solution, respectively. Therefore, the oxalic acid/Nb molar ratio of the aqueous solution was 2.63.

(Preparation of a niobium-containing oxide catalyst: $MO_1V_{0.33}Nb_{0.11}Te_{0.22}O_n$)

TABLE 3

| | Preparation of niobium-containing aqueous solution | | | Niobium-containing aqueous solution | | | Ammoxidation of propane to produce acrylonitrile | | | |
|---|---|---|---|---|---|---|---|---|---|---|
| | Niobium compound | Dicarboxylic acid | Cooling operation | Oxalic acid/Nb (molar ratio) | Ammonia/Nb (molar ratio) | $SiO_2$ content of catalyst*[1] (wt. %) | Type of reactor*[2] | Conversion (%) | Selectivity (%) | Yield (%) |
| Ex. 11 | Niobic acid (B) | Oxalic acid | Conducted [Method (A)] | 2.6 | 0 | 30 | Fluidized-bed reactor | 83.0 | 57.5 | 47.7 |
| Ex. 12 | Niobic acid (B) | Oxalic acid | Conducted [Method (A)] | 3.0 | 0 | 30 | Fluidized-bed reactor | 84.9 | 60.2 | 51.1 |
| Ex. 13 | Niobium hydrogen-oxalate | — | Conducted [Method (A)] | 3.0 | 0 | 30 | Fluidized-bed reactor | 85.1 | 59.7 | 50.8 |
| Comp. Ex. 8 | Niobic acid (B) | Oxalic acid | Not conducted | 5.5 | 0 | 30 | Fluidized-bed reactor | 74.2 | 52.3 | 38.8 |
| Ex. 14 | Niobic acid (B) | Oxalic acid | Conducted [Method (A)] | 2.8 | 0 | 30 | Fluidized-bed reactor | 84.1 | 59.7 | 50.2 |
| Ex. 15 | Niobic acid (B) | Oxalic acid | Conducted [Method (A)] | 3.0 | 0 | 30 | Fluidized-bed reactor | 84.5 | 60.3 | 51.0 |
| Ex. 16 | Niobic acid (B) | Oxalic acid | Conducted [Method (A)] | 3.0 | 0 | 50 | Fluidized-bed reactor | 76.8 | 58.8 | 45.2 |
| Comp. Ex. 9 | Niobic acid (B) | Oxalic acid | Not conducted | 5.5 | 0 | 50 | Fluidized-bed reactor | 61.8 | 40.2 | 24.8 |
| Ex. 17 | Niobic acid (B) | Oxalic acid | Conducted [Method (A)] | 2.6 | 0 | 0 | Fixed-bed reactor | 88.4 | 60.1 | 52.9 |

Notes:
*[1] Catalyst: $Mo_1V_{0.32}Nb_{0.12}Te_{0.22}O_n/SiO_2$
*[2] Reaction conditions for ammoxidation using fluidized-bed rector (inner diameter: 25 mm): temperature = 430° C.; pressure = atmospheric pressure; contact time = 3.0 sec · g/cc; [propane:ammonia:oxygen:helium] molar ratio = 1:1.2:3:12
Reaction conditions for ammoxidation using fixed-bed rector (inner diameter: 10 mm): temperature = 430° C.; pressure = atmospheric pressure; contact time = 1.0 sec · g/cc; [propane:ammonia:oxygen:helium] molar ratio = 1:1.2:3:12

To 80 g of water were added 20.00 g of ammonium heptamolybdate [$(NH_4)_6Mo_7O_{24} \cdot 4H_2O$], 4.37 g of ammonium metavanadate ($NH_4VO_3$) and 5.72 g of telluric acid ($H_6TeO_6$), while stirring at 60° C., followed by cooling to 30° C., to thereby obtain an aqueous solution.

To the obtained aqueous solution was added 27.09 g of the niobium-containing aqueous solution (E-18), while stirring for about 30 minutes, thereby obtaining an aqueous compound mixture.

The obtained aqueous compound mixture was sprayed onto a Teflon-coated steel plate having a temperature of 140° C., to thereby obtain a dried particulate catalyst precursor.

3 g of the obtained catalyst precursor was charged into a quartz tube (inner diameter: 20 mm) and calcined at 600° C. for 2 hours under a stream of nitrogen gas at a flow rate of 300 Ncc/min, to thereby obtain a niobium-containing oxide catalyst. The oxygen concentration of the nitrogen gas determined by means of a trace oxygen analyzer (Type: 306 WA, manufactured and sold by Teledyne Analytical Instruments, U.S.A.) was 1 ppm.

(Ammoxidation of propane)

10 0.3 g of the catalyst obtained above was charged into a fixed-bed reaction tube having an inner diameter of 4 mm. A gaseous mixture having a (propane, ammonia, oxygen and helium) molar ratio of 1:1.2:3:14.8 was fed into the reaction tube at a flow rate of 0.100 Ncc/sec, to thereby effect an ammoxidation of propane to produce acrylonitrile. The reaction temperature was 420° C., and the reaction pressure was atmospheric pressure. The contact time was 1.2 sec·g/cc. The results of the ammoxidation are shown in Table 4, together with the composition of the niobium-containing aqueous solution used for producing the catalyst.

EXAMPLE 19
[Preparation of a niobium-containing aqueous solution by method (B) (insoluble Nb compound removal method)]

The obtained aqueous semisolution was subjected to suction filtration using a filter paper ("No. 101<135 mm>; quantity 100" manufactured and sold by TOYO ROSHI KAISHA Ltd., Japan), to thereby obtain a niobium-containing aqueous solution (E-19) and a filtration residue containing suspended niobic acid. The niobium concentration and oxalic acid concentration of the obtained aqueous solution were determined in accordance with the method described in Example 11. As a result, it was found that the niobium concentration and oxalic acid concentration of the obtained aqueous solution were 0.386 mol/kg of the aqueous solution and 1.05 mol/kg of the aqueous solution, respectively. Therefore, the oxalic acid/Nb molar ratio of the aqueous solution was 2.71.

All of the obtained filtration residue was added to a crucible and dried at 120° C. for 2 hours, followed by calcination at 850° C. for 2 hours, thereby obtaining 3.20 g of niobium oxide. As a result, it was found that the weight percentage of the suspended niobic acid was 7.90% by weight in terms of the amount of $Nb_2O_5$, based on the total weight of the dissolved niobic acid and the suspended niobic acid, each in terms of the amount of $Nb_2O_5$.

(Preparation of a niobium-containing oxide catalyst: $Mo_1V_{0.33}Nb_{0.11}Te_{0.22}O_n$)

A niobium-containing oxide catalyst was prepared in substantially the same manner as in Example 18, except that 32.31 g of the niobium-containing aqueous solution (E-19) was used instead of 27.09 g of the niobium-containing aqueous solution (E-18).

(Ammoxidation of propane)

The ammoxidation of propane was performed in substantially the same manner as in Example 18, except that the oxide catalyst prepared above was used instead of the oxide catalyst prepared in Example 18. The results of the ammoxidation are shown in Table 4, together with the composition of the niobium-containing aqueous solution used for producing the catalyst.

TABLE 4

| | Preparation of niobium-containing aqueous solution | | | | Niobium-containing aqueous solution | | | | Ammoxidation of propane for producing acrylonitrile | | |
|---|---|---|---|---|---|---|---|---|---|---|---|
| | Niobium compound | Dicarboxylic acid | Cooling operation | Separation of suspended Nb | Suspended Nb/total Nb used (wt. %) | Oxalic acid/Nb (molar ratio) | Ammonia Nb (molar ratio) | $SiO_2$ content of catalyst*[1] (wt. %) | Type of reactor*[2] | Conversion (%) | Selectivity (%) | Yield (%) |
| Ex. 18 | Niobic acid (C) | Oxalic acid | Conducted [Method (A)] | — | — | 2.63 | 0 | 0 | Fixed-bed-reactor | 89.8 | 61.1 | 54.9 |
| Ex. 19 | Niobic acid (C) | Oxalic acid | Not conducted | Conducted [Method (B)] | 7.90 | 2.71 | 0 | 0 | Fixed-bed reactor | 90.5 | 61.1 | 55.3 |

Notes:
*[1] Catalyst: $Mo_1V_{0.33}Nb_{0.11}Te_{0.22}O_n$
*[2] Reaction conditions for ammoxidation using fixed-bed rector (inner diameter: 4 mm): temperature = 420° C.; pressure = atmospheric pressure; contact time = 1.2 sec · g/cc; [propane:ammonia:oxygen:helium] molar ratio = 1:1.2:3:14.8

To 582 g of water was added 96.03 g of oxalic acid ($H_2C_2O_4 \cdot 2H_2O$), while stirring at about 70° C., to thereby obtain an oxalic acid solution. To the obtained oxalic acid solution was added 54.00 g of niobic acid (C) ($Nb_2O_5$ content: 75.0% by weight), while stirring at about 70° C. for 1 hour, followed by cooling to about 30° C., thereby obtaining a niobium-containing aqueous semisolution having suspended therein a part of the niobic acid. An oxalic acid/Nb molar ratio of the obtained semisolution was 2.50.

EXAMPLE 20
[Preparation of a niobium-containing aqueous solution by method (C) (acidic solution-basic compound method)]

To 800 g of water was added 302.14 g of oxalic acid ($H_2C_2O_4 \cdot 2H_2O$), while stirring at about 70° C., to thereby obtain an aqueous oxalic acid solution. To the obtained oxalic acid solution was added 50.0 g of niobic acid (C) ($Nb_2O_5$ content: 75.0% by weight), and the resultant solution was stirred at about 70° C. for 1 hour, followed by cooling to about 30° C., thereby obtaining an aqueous acidic semisolution having suspended therein a part of the niobic acid. The oxalic acid/Nb molar ratio of the aqueous acidic semisolution was 8.50.

The suspended niobic acid was removed from the aqueous acidic semisolution by suction filtration using a filter paper ("No. 101<135 mm>; quantity 100" manufactured and sold by TOYO ROSHI KAISHA Ltd., Japan), to thereby obtain a niobium-containing aqueous acidic solution and a filtration residue containing suspended the niobic acid thus removed.

All of the obtained filtration residue was placed in a crucible and dried at 120° C. for 2 hours, followed by calcination at 850° C. for 2 hours in the air, thereby obtaining 0.50 g of a niobium oxide. It was found that the weight percentage of the suspended niobium compound (removed by suction filtration) was 1.33% by weight in terms of the amount of $Nb_2O_5$, based on the total weight of the dissolved niobic acid and the suspended niobic acid, each in terms of the amount of $Nb_2O_5$.

To the obtained aqueous acidic solution was added aqueous ammonia ($NH_3$ content: 25% by weight) in an amount such that the pH of the resultant mixture became 9, to thereby precipitate the niobium in the form of a niobic acid.

The precipitated niobic acid was recovered by suction filtration using a filter paper ("No. 101<135 mm>; quantity 100" manufactured and sold by TOYO ROSHI KAISHA Ltd., Japan). The recovered niobic acid was washed 5 times with 300 ml of water, and then dried at 70° C. for 2.5 hours in a vacuum dryer, to thereby obtain a dried niobic acid.

1.000 g of the obtained dried niobic acid was placed in a crucible and calcined for 2 hours at 850° C. in the air, to thereby obtain 0.470 g of $Nb_2O_5$. It was found that the $Nb_2O_5$ content of the dried niobic acid before calcination was 47.0% by weight.

To 24.6 g of water were added 3.52 g of the obtained niobic acid and 4.23 g of oxalic acid ($H_2C_2O_4.2H_2O$), and the resultant mixture was stirred at about 60° C. for 1 hour, followed by cooling to about 30° C., thereby obtaining a niobium-containing aqueous solution (E-20) having an oxalic acid/Nb molar ratio of 2.70.

(Preparation of a niobium-containing oxide catalyst: $Mo_1V_{0.33}Nb_{0.11}Te_{0.22}O_n$)

A niobium-containing oxide catalyst was prepared in substantially the same manner as in Example 18, except that a whole amount of the niobium-containing aqueous solution (E-20) thus obtained was used instead of 27.09 g of the niobium-containing aqueous solution (E-18).

(Ammoxidation of propane)

The ammoxidation of propane was performed in substantially the same manner as in Example 18, except that the oxide catalyst prepared above was used instead of the oxide catalyst prepared in Example 18. The results of the ammoxidation are shown in Table 5, together with the composition of the niobium-containing aqueous solution used for producing the catalyst.

EXAMPLE 21

[Preparation of a niobium-containing aqueous solution by method (C) (acidic solution-basic compound method)]

To 1,200 g of water was added 392.0 g of tartaric acid ($H_6C_4O_6$), while stirring at about 80° C., to thereby obtain an aqueous tartaric acid solution. To the obtained tartaric acid solution was added 50.0 g of niobic acid (C) ($Nb_2O_5$ content: 75.0% by weight), and the resultant mixture was stirred at about 80° C. for 1 hour, followed by cooling to about 30° C., thereby obtaining an aqueous acidic semisolution having suspended therein a part of the niobic acid. The tartaric acid/Nb molar ratio of the aqueous acidic semisolution was 9.26.

The suspended niobic acid was removed from the aqueous acidic semisolution by suction filtration using a filter paper ("No. 101<135 mm>; quantity 100" manufactured and sold by TOYO ROSHI KAISHA Ltd., Japan), to thereby obtain a niobium-containing aqueous acidic solution and a filtration residue containing the niobic acid thus removed.

All of the obtained filtration residue was placed in a crucible and dried at 120° C. for 2 hours, followed by calcination at 850° C. for 2 hours in the air, thereby obtaining 1.60 g of a niobium oxide. It was found that the weight percentage of the suspended niobic acid was (removed by suction filtration) 4.27% by weight in terms of the amount of $Nb_2O_5$, based on the total weight of the dissolved niobic acid and the suspended niobic acid, each in terms of the amount of $Nb_2O_5$.

To the obtained aqueous acidic solution was added aqueous ammonia ($NH_3$ content: 25% by weight) in an amount such that the pH of the resultant mixture became 9, to thereby precipitate the niobium in the form of a niobic acid.

The precipitated niobic acid was recovered by suction filtration using a filter paper ("No. 101<135 mm>; quantity 100" manufactured and sold by TOYO ROSHI KAISHA Ltd., Japan). The recovered niobic acid was washed 5 times with 300 ml of water, and then dried at 70° C. for 2.5 hours in a vacuum dryer, to thereby obtain a dried niobic acid.

1.000 g of the obtained dried niobic acid was placed in a crucible and calcined for 2 hours at 850° C. in the air, to thereby obtain 0.475 g of $Nb_2O_5$. It was found that the $Nb_2O_5$ content of the dried niobic acid before calcination was 47.5% by weight.

To 24.6 g of water were added 3.48 g of the obtained niobic acid and 4.23 g of oxalic acid ($H_2C_2O_4.2H_2O$), and the resultant mixture was stirred at about 60° C. for 1 hour, followed by cooling to about 30° C., thereby obtaining a niobium-containing aqueous solution (E-20) having an oxalic acid/Nb molar ratio of 2.70.

(Preparation of a niobium-containing oxide catalyst: $Mo_1V_{0.33}Nb_{0.11}Te_{0.22}O_n$)

A niobium-containing oxide catalyst was obtained in substantially the same manner as in Example 18, except that a whole amount of the niobium-containing aqueous solution (E-21) thus obtained was used instead 27.09 g of the niobium-containing aqueous solution (E-18).

(Ammoxidation of propane)

The ammoxidation of propane was performed in substantially the same manner as in Example 18, except that the oxide catalyst prepared above was used instead of the oxide catalyst prepared in Example 18. The results of the ammoxidation are shown in Table 5, together with the composition of the niobium-containing aqueous solution used for producing the catalyst.

EXAMPLE 22

[Preparation of a niobium-containing aqueous solution) by method (D) (basic solution-acidic compound method)]

Into a 1-liter autoclave having a Teflon inner lining were added 300 g of water, 8.0 g of niobic acid (C) ($Nb_2O_5$ content: 75.0% by weight) and 60.0 g of potassium hydroxide (KOH), and after sealing the autoclave, the resultant mixture was heated at 200° C. for 15 hours, while stirring. The autoclave was cooled, and then, an aqueous basic semisolution having suspended therein a part of the niobic acid was taken from the autoclave.

The suspended niobic acid was removed from the aqueous basic semisolution by suction filtration using a filter paper ("No. 101<135 mm>; quantity 100" manufactured and sold by TOYO ROSHI KAISHA Ltd., Japan), to thereby obtain a niobium-containing aqueous basic solution and a filtration residue containing the niobic acid thus removed.

All of the obtained filtration residue was placed in a crucible and dried at 120° C. for 2 hours, followed by calcination at 850° C. for 2 hours in the air, thereby obtaining 0.16 g of a niobium oxide. It was found that the weight percentage of the suspended niobic acid (removed by suction filtration) was 2.67% by weight in terms of the amount of $Nb_2O_5$, based on the total weight of the dissolved niobic acid and the suspended niobic acid, each in terms of the amount of $Nb_2O_5$.

To the obtained aqueous basic solution was added concentrated nitric acid in an amount such that the pH of the resultant mixture became 7, to thereby precipitate the niobium in the form of a niobic acid.

The precipitated niobic acid was recovered by suction filtration using a filter paper ("No. 101<135 mm>; quantity 100" manufactured and sold by TOYO ROSHI KAISHA Ltd., Japan). The recovered niobic acid was washed 5 times with 300 ml of water, and then dried at 70° C. for 2.5 hours in a vacuum dryer, to thereby obtain a dried niobic acid.

1.000 g of the obtained niobic acid was placed in a crucible and calcined for 2 hours at 850° C. in the air, to thereby obtain 0.480 g of $Nb_2O_5$. It was found that the $Nb_2O_5$ content of the dried niobic acid before calcination was 48.0% by weight.

To 24.6 g of water were added 3.45 g of the obtained niobic acid and 4.24 g of oxalic acid ($H_2C_2O_4 \cdot 2H_2O$), and the resultant mixture was stirred at about 60° C. for 1 hour, followed by cooling to about 30° C., thereby obtaining a niobium-containing aqueous solution (E-22) having an oxalic acid/Nb molar ratio of 2.70.

(Preparation of a niobium-containing oxide catalyst: $Mo_1V_{0.33}Nb_{0.11}Te_{0.22}O_n$)

A niobium-containing oxide catalyst was prepared in substantially the same manner as in Example 18, except that a whole amount of the niobium-containing aqueous solution (E-22) was used instead of 27.09 g of the niobium-containing aqueous solution (E-18).

(Ammoxidation of propane)

The ammoxidation of propane was performed in substantially the same manner as in Example 18, except that the oxide catalyst prepared above was used instead of the oxide catalyst prepared in Example 18. The results of the ammoxidation are shown in Table 5, together with the composition of the niobium-containing aqueous solution used for producing the catalyst.

TABLE 5

| | Preparation of niobic acid | | | | Niobium-containing aqueous solution | | SiO$_2$ | Ammoxidation of propane for producing acrylonitrile | | | |
|---|---|---|---|---|---|---|---|---|---|---|---|
| | Niobium compound | Aqueous acidic or basic solution | Precipitant | Separation of suspended Nb | Suspended Nb/total Nb used (wt. %) | Oxalic acid/Nb (molar ratio) | Ammonia/Nb (molar ratio) | content of catalyst*1) (wt. %) | Type of reactor*2 | Conversion (%) | Selectivity (%) | Yield (%) |
| Ex. 20 | Niobic acid (C) | Oxalic acid [Method (C)] | Aqueous ammonia | Conducted | 1.33 | 2.70 | 0 | 0 | Fixed-bed reactor | 90.7 | 61.1 | 55.4 |
| Ex. 21 | Niobic acid (C) | Tartaric acid [Method (C)] | Aqueous ammonia | Conducted | 4.27 | 2.70 | 0 | 0 | Fixed-bed reactor | 90.6 | 61.2 | 55.4 |
| Ex. 22 | Niobic acid (C) | KOH [Method (D)] | Concentrated nitric acid | Conducted | 2.67 | 2.70 | 0 | 0 | Fixed-bed reactor | 89.8 | 60.7 | 54.5 |

Notes:
*1)Catalyst: $Mo_1V_{0.33}Nb_{0.11}Te_{0.22}O_n$
*2)Reaction conditions for ammoxidation using fixed-bed rector (inner diameter: 4 mm): temperature = 420° C.; pressure = atmospheric pressure; contact time = 1.2 sec · g/cc; [propane:ammonia:oxygen:helium] molar ratio = 1:1.2:3:14.8

INDUSTRIAL APPLICABILITY

By the use of the niobium-containing aqueous solution of the present invention, it has become possible to produce efficiently an oxide catalyst which, when used in a catalytic oxidation or ammoxidation of propane or isobutane in the gaseous phase, exhibits high catalytic activity. Therefore, by the use of the oxide catalyst produced by using the niobium-containing aqueous solution of the present invention, (meth) acrylic acid or (meth)acrylonitrile can be produced in high yield. Further, even when the oxide catalyst is in a silica-supported form, the oxide catalyst does not suffer a lowering of the catalytic activity, differing from the conventional silica-supported oxide catalysts for use in a catalytic oxidation or ammoxidation of propane or isobutane in the gaseous phase.

We claim:

1. A niobium-containing aqueous solution for use in producing a niobium-containing oxide catalyst, wherein said niobium-containing oxide catalyst comprises an oxide of a plurality of active component elements including niobium and is for use in a catalytic oxidation or ammoxidation of propane or isobutane in the gaseous phase, and wherein said niobium-containing oxide catalyst is prepared by a process comprising mixing said niobium-containing aqueous solution with an aqueous mixture or aqueous mixtures containing compounds of active component elements of said oxide catalyst other than niobium, to thereby provide an aqueous compound mixture, and drying said aqueous compound mixture, followed by calcination, said niobium-containing aqueous solution comprising water having dissolved therein a dicarboxylic acid, a niobium compound and optionally ammonia, wherein the molar ratio (α) of said dicarboxylic acid to the niobium contained in said niobium compound satisfies the following relationship: $1 \leq (\alpha) \leq 4$, and the molar ratio ($\beta$) of said ammonia to the niobium contained in said niobium compound satisfies the following relationship: $0 \leq (\beta) \leq 2$.

2. The niobium-containing aqueous solution according to claim 1, wherein the molar ratio ($\alpha$) of said dicarboxylic acid to the niobium contained in said niobium compound satisfies the following relationship: $2 \leq (\alpha) \leq 4$, and the molar ratio ($\beta$) of said ammonia to the niobium contained in said niobium compound satisfies the following relationship: $0 \leq (\beta) \leq 1$.

3. The niobium-containing aqueous solution according to claim 1, wherein said active component elements of the niobium-containing oxide catalyst are niobium, molybdenum, vanadium, and at least one element selected from the group consisting of tellurium and antimony.

4. The niobium-containing aqueous solution according to claim 1, which is prepared by a process comprising:

(i) mixing water, a dicarboxylic acid and a niobium compound to thereby obtain a preliminary niobium-containing aqueous solution or a niobium-containing aqueous semisolution having suspended therein a part of said niobium compound;

(ii) cooling said preliminary niobium-containing aqueous solution or niobium-containing aqueous semisolution to thereby precipitate a part of said dicarboxylic acid; and (iii) removing the precipitated dicarboxylic acid from said preliminary niobium-containing aqueous solution, or removing the precipitated dicarboxylic acid and the suspended niobium compound from said niobium-containing aqueous semisolution, thereby obtaining a niobium-containing aqueous solution.

5. The niobium-containing aqueous solution according to claim 1, which is prepared by a process comprising:

(i) mixing water, a dicarboxylic acid and a niobium compound to thereby obtain a niobium-containing aqueous semisolution having suspended therein a part of said niobium compound; and (ii) removing the suspended niobium compound from said niobium-containing aqueous semisolution, thereby obtaining a niobium-containing aqueous solution.

6. The niobium-containing aqueous solution according to claim 1, which is prepared by a process comprising:

(i) adding a niobium compound to an aqueous acidic solution to thereby obtain a niobium-containing aqueous acidic semisolution having suspended therein a part of said niobium compound;

(ii) removing the suspended niobium compound from said niobium-containing aqueous acidic semisolution to thereby obtain a niobium-containing aqueous acidic solution;

(iii) adding a basic compound to said niobium-containing aqueous acidic solution to precipitate the niobium in the form of a niobic acid;

(iv) recovering the precipitated niobic acid; and (v) dissolving said niobic acid in a mixture of water and a dicarboxylic acid, thereby obtaining a niobium-containing aqueous solution.

7. The niobium-containing aqueous solution according to claim 1, which is prepared by a process comprising:

(i) adding a niobium compound to an aqueous basic solution to thereby obtain a niobium-containing aqueous basic semisolution having suspended therein a part of said niobium compound;

(ii) removing the suspended niobium compound from said niobium-containing aqueous basic semisolution to thereby obtain a niobium-containing aqueous basic solution;

(iii) adding an acidic compound to said niobium-containing aqueous basic solution to precipitate the niobium in the form of a niobic acid;

(iv) recovering the precipitated niobic acid; and (v) dissolving said niobic acid in a mixture of water and a dicarboxylic acid, thereby obtaining a niobium-containing aqueous solution.

8. The niobium-containing aqueous solution according to claim 4, wherein said niobium compound is at least one compound selected from the group consisting of a niobic acid and niobium hydrogen-oxalate, and said dicarboxylic acid is oxalic acid.

9. A niobium-containing oxide catalyst for use in a catalytic oxidation or ammoxidation of propane or isobutane in the gaseous phase, comprising an oxide of a plurality of active component elements including niobium, wherein said niobium-containing oxide catalyst is prepared by a process comprising mixing a niobium-containing aqueous solution with an aqueous mixture or aqueous mixtures containing compounds of active component elements of said oxide catalyst other than niobium, to thereby provide an aqueous compound mixture, and drying said aqueous compound mixture, followed by calcination, said niobium-containing aqueous solution comprising water having dissolved therein a dicarboxylic acid, a niobium compound and optionally ammonia, wherein the molar ratio ($\alpha$) of said dicarboxylic acid to the niobium contained in said niobium compound satisfies the following relationship: $1 \leq (\alpha) \leq 4$, and the molar ratio ($\beta$) of said ammonia to the niobium contained in said niobium compound satisfies the following relationship: $0 \leq (\beta) \leq 2$.

10. The oxide catalyst according to claim 9, wherein said active component elements are niobium, molybdenum, vanadium, and at least one element selected from the group consisting of tellurium and antimony.

11. The oxide catalyst according to claim 9, which further comprises a silica carrier having supported thereon said oxide of a plurality of active component elements, wherein said silica carrier is present in an amount of from 20 to 70% by weight, based on the total weight of said oxide and said silica carrier.

12. A process for producing a niobium-containing oxide catalyst for use in a catalytic oxidation or ammoxidation of propane or isobutane in the gaseous phase, wherein said niobium-containing oxide catalyst comprises an oxide of a plurality of active component elements including niobium, said process comprising mixing a niobium-containing aqueous solution with an aqueous mixture or aqueous mixtures containing compounds of active component elements of said oxide catalyst other than niobium, to thereby provide an aqueous compound mixture, and drying said aqueous compound mixture, followed by calcination, said niobium-containing aqueous solution comprising water having dissolved therein a dicarboxylic acid, a niobium compound and optionally ammonia, wherein the molar ratio ($\alpha$) of said dicarboxylic acid to the niobium contained in said niobium compound satisfies the following relationship: $1 \leq (\alpha) \leq 4$, and the molar ratio (β) of said ammonia to the niobium contained in said niobium compound satisfies the following relationship: $0 \leq (\beta) \leq 2$.

13. The process according to claim 12, wherein said active component elements are niobium, molybdenum, vanadium, and at least one element selected from the group consisting of tellurium and antimony.

14. The process according to claim 12, wherein said aqueous compound mixture is provided so as to further contain a silica sol in an amount such that said oxide catalyst further comprises a silica carrier in an amount of from 20 to 70% by weight, based on the total amount of said oxide and said silica carrier, said silica carrier having supported thereon said oxide of a plurality of active component elements.

15. A process for producing acrylic acid or methacrylic acid from propane or isobutane by oxidation in the gaseous phase, comprising:

provinding a niobium-containing oxide catalyst comprising an oxide of a plurality of active component elements including niobium, wherein said niobium-containing oxide catalyst is prepared by a process comprising mixing a niobium-containing aqueous solution with an aqueous mixture or aqueous mixtures containing compounds of active component elements of said oxide catalyst other than niobium, to thereby provide an aqueous compound mixture, and drying said aqueous compound mixture, followed by calcination, said niobium-containing aqueous solution comprising water having dissolved therein a dicarboxylic acid, a niobium compound and optionally ammonia, wherein the molar ratio (α) of said dicarboxylic acid to the niobium contained in said niobium compound satisfies the following relationship: $1 \leq (\alpha) \leq 4$, and the molar ratio (β) of said ammonia to the niobium contained in said niobium compound satisfies the following relationship: $0 \leq (\beta) \leq 2$; and reacting propane or isobutane with molecular oxygen in the gaseous phase in the presence of said niobium-containing oxide catalyst.

16. The process according to claim 15, wherein said active component elements of the niobium-containing oxide catalyst are niobium, molybdenum, vanadium, and at least one element selected from the group consisting of tellurium and antimony.

17. The process according to claim 15, wherein said niobium-containing oxide catalyst further comprises a silica carrier having supported thereon said oxide of a plurality of active component elements, wherein said silica carrier is present in an amount of from 20 to 70% by weight, based on the total weight of said oxide and said silica carrier.

18. A process for producing acrylonitrile or methacrylonitrile from propane or isobutane by ammoxidation in the gaseous phase, comprising:

providing a niobium-containing oxide catalyst comprising an oxide of a plurality of active component elements including niobium, wherein said niobium-containing oxide catalyst is prepared by a process comprising mixing a niobium-containing aqueous solution with an aqueous mixture or aqueous mixtures containing compounds of active component elements of said oxide catalyst other than niobium, to thereby provide an aqueous compound mixture, and drying said aqueous compound mixture, followed by calcination, said niobium-containing aqueous solution comprising water having dissolved therein a dicarboxylic acid, a niobium compound and optionally ammonia, wherein the molar ratio (α) of said dicarboxylic acid to the niobium contained in said niobium compound satisfies the following relationship: $1 \leq (\alpha) \leq 4$, and the molar ratio (β) of said ammonia to the niobium contained in said niobium compound satisfies the following relationship: $0 \leq (\beta) \leq 2$; and reacting propane or isobutane with ammonia and molecular oxygen in the gaseous phase in the presence of said niobium-containing oxide catalyst.

19. The process according to claim 18, wherein said active component elements of the niobium-containing oxide catalyst are niobium, molybdenum, vanadium, and at least one element selected from the group consisting of tellurium and antimony.

20. The process according to claim 18, wherein said niobium-containing oxide catalyst further comprises a silica carrier having supported thereon said oxide of a plurality of active component elements, wherein said silica carrier is present in an amount of from 20 to 70% by weight, based on the total weight of said oxide and said silica carrier.

* * * * *